United States Patent [19]
Bakis et al.

[11] Patent Number: 5,851,461
[45] Date of Patent: Dec. 22, 1998

[54] METHOD OF PRODUCING POLYSACCHARIDE FOAMS

[75] Inventors: George Bakis, West Roxbury; Dana Burton Eagles, Sherborn; John F. Tweedie, Winchester, all of Mass.

[73] Assignee: Albany International Research Co., Mansfield, Mass.

[21] Appl. No.: 801,098

[22] Filed: Feb. 14, 1997

Related U.S. Application Data

[63] Continuation of Ser. No. 487,447, filed as PCT/US93/05993 Jun. 18, 1993, abandoned.

[30] Foreign Application Priority Data

Jun. 19, 1992 [GB] United Kingdom .................... 9212976
Nov. 19, 1992 [GB] United Kingdom .................. 92242551

[51] Int. Cl.$^6$ ...................................................... B29D 1/00
[52] U.S. Cl. .............................. 264/50; 156/78; 156/305; 156/306.3; 428/316.6
[58] Field of Search ......................... 156/78, 305, 306.3; 264/50; 428/316.6

[56] References Cited

U.S. PATENT DOCUMENTS

| | | | |
|---|---|---|---|
| 2,133,805 | 10/1938 | Brown | 428/316.6 |
| 3,081,181 | 3/1963 | Rutenberg et al. | 264/50 |
| 3,634,183 | 1/1972 | Viola et al. | 156/306.3 |

FOREIGN PATENT DOCUMENTS

| | | | |
|---|---|---|---|
| 560317 | 3/1944 | United Kingdom | 264/50 |

*Primary Examiner*—John J. Gallagher
*Attorney, Agent, or Firm*—Kane, Dalsimer, Sullivan, Kuruz, Levy, Eisele and Richard

[57] ABSTRACT

Disclosed is a method of producing polysaccharide foams and foams produced by the method. The polysaccharide foams are formed from a wet condition and are convection dried with a flow of warm or hot air. Such foams exhibit improvements over foams dried under ambient conditions. The present invention also discloses the formation of multi-ply foam layers. At least two sheets of foam layers are layered together and laminated either mechanically or chemically to produce a composite structure.

9 Claims, 14 Drawing Sheets

METHOD OF PRODUCING POLYSACCHARIDE FOAMS

This application is a continuation of application Ser. No. 08/487,447, filed as PCT/US93/05993 Jun. 18, 1993, now abandoned.

DESCRIPTION

The present invention relates to a method of producing polysaccharide foams; in particular alginate, chitosan, starch and hyaluronate foams. The invention also embraces polysaccharide foamed materials produced in accordance with the method of the invention and wound dressings, foamed cell culture replicating media, barrier media for preventing tissue adherence and other absorbent materials comprising such foams.

Alginates, particularly calcium alginates and converted calcium alginates, have long been known for their ability to form fibers and yarns which can be knitted into fabrics or formed into non-woven materials primarily for use as swabs or dressing for medical, surgical or other purposes.

For instance, British Patent Specification No. 1283399 describes and claims a method of preparing a solubilized calcium-containing alginate material which comprises acidifying calcium alginate with a calculated quantity of acid sufficient to remove a desired amount of calcium, reacting the acidified calcium alginate with an excess of base selected from ammonia, amines and substituted amines and washing the solubilized calcium-containing alginate to remove the excess base.

This material may be formed into a number of pieces of gauze which can then be further treated as described in the specification.

British Patent Specification No. 1394742 relates to a surgical dressing material comprising a layer of knitted gauze adhered to a layer of fibrous backing material, the gauze comprising alginate material and the dressing material being of lower flexibility and stretchability than the gauze itself.

British Patent Specification No. 1570485 relates to an absorbent material for aqueous fluids which comprises an open cell foam containing within the cells a hydrophilic gel having specific properties. Typical of the hydrophilic gels is alginates. The specification, describes the incorporation of these materials in a reticulated foam; the gel being contained within the cells of the foam thus providing an absorbent material.

U.S. Pat. No. 4,421,583 relates to a non-woven alginate fabric useful as a wound dressing made by spreading a tow of calcium alginate filaments into a flow of water, overfeeding the spread filaments onto a water pervious support so that the filaments cross over each other, and drying the filaments so that they become bonded to each other at their points of contact where they cross over. The filaments used have preferably been pre-stretched in atmosphere of steam and wash water and not dried and are preferably subsequently dried by suction on the water pervious support.

U.S. Pat. No. 4,793,337 discloses an improved adhesive structure for adhesion of an article to a fluid emitting wound, the structure having an absorbent region comprising an absorbent fibrous fabric or foam material intermediate first and second contact regions, whereby enhanced cohesion between the first and second regions and between the second region and the article under conditions of heavy fluid emission is provided. This specification discloses the use of sodium alginate in combination with a calcium powder by way of absorbent material.

U.S. Pat. No. 4,948,575 discloses a dimensionally stable alginate hydrogel foam wound dressing that absorbs wound exudate without any appreciable swelling. The wound dressing includes alkaline metal earth (except magnesium) salts and Group III metal salts of alginic acid. The hydrogel foam may be formed by mixing together a first liquid component comprising (a) an aqueous suspension of particles of a water insoluble di- or trivalent metal salt and (b) an effervescent compound which effervesces upon reaction with an acid; and a second liquid component comprising an aqueous solution of biocompatible, water-soluble acid wherein at least one of the components further comprises a water-soluble alginate dissolved therein. Upon mixing the water-insoluble metal salt reacts with the water soluble acid to form a water soluble metal salt that is subsequently ionized. The polyvalent cations released from the water-soluble metal salt complex with the carboxylate groups of the water-soluble alginate causing the formation and precipitation of a water insoluble alginate hydrogel. At the same time the effervescent compound is reacting with the water soluble acid; the resultant evolution of gases effects the formation of a stable hydrogel foam.

Commercially available alginate products are marketed inter alia as hemostatic wound dressings using non-woven fibre technology. However, non-woven alginate materials, while performing their function satisfactorily, are difficult to handle. Several attempts have been made to improve handling, for example Swedish patent Application published under No. 424956 describes an alginate hydrogel wound dressing formed on a wound in combination with an elastic rubber-like composition. In another attempt at providing a more readily usable material, it has been proposed to use a freeze-dried foam as disclosed in U.S. Pat. No. 4,642,903. The disadvantage of all these prior art foam methods is that there is little or no control over the foam size and that the resultant products are relatively difficult to handle.

SUMMARY OF THE INVENTION

According to one aspect of the present invention, therefore, there is provided a method of forming a polysaccharide foam which comprises preparing an aqueous solution including a soluble polysaccharide and thereafter mechanically foaming the solution.

The present invention is directed to a method of forming a polysaccharide foam from an aqueous solution of a polysaccharide, consisting essentially of the steps of:

a) forming an aqueous solution of a polysaccharide and a foam stabilizer;

b) introducing a gas into the aqueous solution to form a wet foam;

c) drying the wet foam with heated air to form a dried polysaccharide foam;

d) subsequently cross-linking or coagulating the dried foam to form a water insoluble foam with cross-linking di- or tri-valent cations.

The foam may be produced by beating or otherwise mechanically agitating the material to cause the polysaccharide to foam. The mechanical foaming may involve the introduction of gas into the solution, and shearing of the solution to create a mixing effect which may result in a very fine dispersion of gas bubbles in the solution. In the early stages of mechanical foaming, when the total amount of gas entrained in the solution is small, the gas bubbles may be substantially spherical in shape. As the total volume of gas entrained in the solution increases, the gas bubbles may undergo a transition from the spherical shape to a substantially polyhedral shape, with the solution distributed in thin membranes between adjacent gas bubbles and in ribs or spokes where several gas bubbles come into very close proximity to each other; the result is a foamed polymer having gas dispersed throughout the solution in a cellular structure. It will be appreciated by a person skilled in the art that, in some embodiments of the present invention, the relative violence and/or period of agitation of mechanical action may be used to provide control over the foam pore size. The foam pore size may be controlled in the range of 5–500μ; typically 50–500μ.

Said soluble polysaccharide may be alginic acid or hyaluronic acid. In some embodiments, said soluble polysaccharide may be a soluble polysaccharide salt such, for example, as an alginate or hyaluronate; typically, sodium alginate or sodium hyaluronate may be used. Alternatively, the soluble polysaccharide may be carrageenans, chitosan, starch, or separately, amylose or amylopectin. A person skilled in the art will appreciate that chitosan is soluble in acid, but is insoluble in neutral and basic solutions; on the other hand, starch is soluble in basic solutions. Thus, where chitosan is used in accordance with the present invention, the mechanical foaming step should be conducted in an acidic aqueous solution; where starch is used, foaming should be conducted in aqueous base.

In one aspect of the invention, a foaming agent may be included in the aqueous solution to assist in foaming the solution. The foaming agent may be a surfactant, typically an ionic or non-ionic surfactant. The ionic surfactant may be selected from sodium stearate, sodium dodecyl sulfate, alpha olefin sulfonates (commercially available under the trade name "Siponate 301-10"), sulfoalkyl amide, monocarboxyl coco imidazoline compounds, dicarboxyl coco imidazoline compounds and sulfated fatty polyoxyethylene quaternary nitrogen compounds.

Said non-ionic surfactant may be selected from octylphenol ethyoxylate (commercially available from Rohm & Haas under the trade name TRITON X-100), modified linear aliphatic polyethers and sorbitan esters.

In another aspect of the invention, a plasticizer may be included in the aqueous solution. Said plasticizer may be selected from glycerol, glucose, polyhydric alcohols, triethanolamine and stearates.

In some embodiments, an oligomeric or polymeric foam modifier may be included in the aqueous solution; said foam modifier may be selected from polyethylene glycol, guar gum, albumin, gelatin, carboxymethyl cellulose, hydroxyethyl cellulose, hydroxypropyl cellulose, polyacrylamide, polyacrylic acid, polyvinyl alcohol, polyvinyl pyrrolidone, polyoxazoline and polyethyeneimine. These foam modifiers may be used to improve the flexibility and toughness of the polysaccharide foam.

In a particular aspect of the invention the foam modifier may be polyethylene glycol functionalized with vinyl groups such, for example, as acrylates. After foaming, the functionalized glycol may be polymerized by irradiation (e.g. u.v. or electron) to form a polymer network within the foam; said network may improve the flexibility and toughness of the foam.

In a different aspect of the invention, the aqueous solution of polysaccharide may include a foam stabilizer. Said foam stabilizer may be selected from ammonium stearate, dodecyl alcohol, tetradecanol, hexadecanol, tridecyloxypolyethanol and polyoxyethylated oleylamine.

In some embodiments, the resultant polysaccharide foam, including foam stabilizer, may be air dried after formation.

On drying, the foam material in an interior region of the foam may "collapse" giving the appearance of crushed foam; the cells constituting the foam may distort such that in one dimension each cell may become smaller than in another dimension substantially normal to the one dimension; this change in shape can be described as a sphere distorting in an ellipsoid. When the cells distort in this way, the foam is referred to herein as a "collapsed" foam. The foam material juxtaposed the surface of the foam may maintain its integrity preserving its mean pore size and pore size distribution.

Where the polysaccharide is chitosan which is foamed in an acidic aqueous solution it may be desirable, in some embodiments, to remove the acid after foaming while the foam is still wet since, on drying, any acid present may have an injurious effect on the chitosan foam. Said acid may be removed after foaming by volatilization or neutralization. Typically, the acid may be aqueous acetic acid which may be removed by volatilization.

In another aspect of the invention, the foam may be stabilized by cross-linking or coagulation thereby to provide a dimensionally stable foam. Typically, the foam may be cross-linked or coagulated while wet; where a foam stabilizer is used the foam may be cross-linked or coagulated after initial drying, and the foam may then be redried.

When the polysaccharide is selected from alginic acid, alginate, hyaluronic acid, hyaluronate, and other soluble polysaccharide materials containing exchangeable counter-cations, the cross-linking may be effected by reacting the foamed polysaccharide with di- or tri-valent cations. Said polysaccharide foam may, in some embodiments, be immersed in or sprayed with a solution of the di- or tri-valent cations. Typically, the cations may be selected from $Ca^{2+}$(aq), $Fe^{2+}$(aq) and $Fe^{3+}$(aq).

Alternatively, in some embodiments, an insoluble carbonate or hydrogen carbonate salt having one or more di- or tri-valent cations may be homogeneously dispersed in the foamed polysaccharide, and the foam may be subsequently treated with a strong acid to liberate carbon dioxide as gas and said cations which then cross-link with the polysaccharide to form a dimensionally stable foam structure. The strong acid may have a concentration of up to 1N, typically 0.1–0.2N. Typically, calcium carbonate may be used as an insoluble carbonate salt. This latter method of cross-linking has the advantage that a relatively thick foam may be stabilized uniformly through its thickness; typically a foam thickness of up to about 5 mm may be homogeneously stabilized using this method to provide a stable foam structure.

In a different aspect of the invention, the cross-linked alginate or hyaluronate foam may be "converted" by treatment with an aqueous solution of a reagent having solubilizing mono-valent cations so that a proportion of the cross-linking di- or tri-valent cations in the foam may be replaced by the mono-valent cations, thereby imparting a degree of solubility in the foam; when contacted with water, the converted foam may form a gel. In some embodiments, the degree of conversion may be controlled; typically a small proportion of the cross linking cations may be replaced to provide a lightly gelling foam (when contacted with water). Alternatively, in some embodiments, substantially all the cross-linking cations may be replaced to provide a substantially water soluble foam. The reagent may be selected from sodium acetate and dilute hydrochloric acid. Typically, the treatment may be performed at a pH in the range 4–7.

In a different aspect of the invention, the wet crosslinked and "converted" foam is immersed in alcohol, preferably isopropanol. Upon drying, such immersed foams exhibit increased wettability in aqueous environments.

Where the soluble polysaccharide is chitosan, the foam may be coagulated by treatment with base. Typically, said base may be sodium hydroxide solution. Alternatively, the chitosan foam may be cross-linked by ionic or covalent bonding. Ionic cross-linking may be obtained by treatment with an aqueous solution of polyvalent anions; typically one or more of sodium sulfate, octyl sulfate, lauryl sulfate, hexadecylsulfate, tripolyphosphate, pyrophosphate and octapolyphosphate may be used as a source of polyvalent anions. In other embodiments, covalent cross-linking may be obtained by treating the chitosan foam with one or more dialdehydes e.g. glyoxal, glutaraldehyde and dialdehyde starch.

Where the polysaccharide is starch, the starch foam may be coagulated by treatment with aqueous ammonium sulfate. Alternatively starch foam may be cross-linked by treatment with formaldehyde; this treatment may be performed in the gaseous or liquid state. If the treatment is performed in the liquid state a solution in alcohol may typically be employed.

The cross-linked or coagulated polysaccharide foam may be dried in air. After drying, the dry, cross-linked or coagulated foam may be washed with water and then redried. Washing may be used to remove e.g. any foaming agent or foam stabilizer residual in the foam.

Said aqueous solution of polysaccharide may further comprise one or more ingredients selected from particulate fillers, barium sulfate, pulp-like fibers of cellulose or other fibrous material and moisture retaining or reinforcing filler materials. Where barium sulfate is used, it will be appreciated that the resultant foam may be substantially opaque to x-rays; the foam may therefore be useful as a medical implant in radiography.

In some embodiments, the foam may be bleached. Bleach may be included in the aqueous solution of polysaccharide; typically, the bleach may be selected from hydrogen peroxide and sodium hypochlorite.

The present invention also includes a polysaccharide foam produced in accordance with the method of the invention; the foam can be controlled at various thicknesses, pore sizes and pore size distributions. The foam may be cross-linked or coagulated; the foam may be a soluble foam, an insoluble foam or a "converted" foam having a desired degree of solubility in at least part of the foam. Typically the foam may be an alginate, hyaluronate, chitosan or starch foam.

In another aspect of the invention, the foam, when wet, may be cast as a layer or as a shaped article. Said foam may be cast inter alia in the form of buttons, beads, balls, cylinders or hemispheres. In some embodiments, the foam may be cast in the shape of a part of a human or animal body e.g. in the shape of an ear or nose.

In a particular aspect of the invention, the foam may be cast as a layer on a substrate. Said substrate may be a woven or non-woven fibrous article, a film or a foam. In some embodiments, the substrate may comprise an assemblage of polysaccharide fibers or yarns. In a particular aspect of the invention the substrate may comprise another layer of polysaccharide foam in accordance with the invention. Said other layer foam may have a different mean pore size and/or pore size distribution from the first mentioned foam.

The foam may be cast as a thin foam layer having a thickness up to about 1 mm. Alternatively, the foam in accordance with the present invention may be cast as a thick foam layer having a thickness of up to about 50 mm. Said thick foam layer may have an interior layer of "collapsed" foam; the foam juxtaposed the surface of the foam may be not significantly collapsed, being similar in appearance and having a pore size and pore size distribution about equal to the foam when freshly formed.

According to another aspect of the invention, the polysaccharide foams are convection dried with a flow of warm or hot air. By drying in this manner a foam structure having a bulk density less than that of foam dried in ambient conditions is realized. Moreover, the foams produced by warm air convection drying exhibit a greater capacity for serum uptake on a gram-serum/gram-alginate basis than commercially available alginate fiber products. Other advantages exhibited by convention dried foams include more uniform pore size, and smaller pores.

The convection dried alginate foam products of the present invention also exhibit superior dry strengths and wet strengths to alginate fiber products known in the art.

The present invention also includes a wound dressing comprising a polysaccharide foam produced by the method in accordance with the present invention. Typically the wound dressing may comprise a layer of said polysaccharide foam. In some embodiments the foam may be disposed on a substrate, the substrate may be a polysaccharide fabric or composed of polysaccharide yarn.

The present invention also includes multi-ply converted and cross-linked foam layers. At least two sheets of alginate foam layers are layered together and laminated either mechanically or chemically to produce a composite structure.

The present invention also includes a cell culture replicating medium comprising a polysaccharide foam produced in accordance with the present invention; the cells to be replicated can be disposed in the pores in the foam to locate the cells.

In some embodiments, the cell culture replicating medium may constitute an implant, typically a bio-absorbable implant.

Cultured cells, e.g. mammalizing cells, may be disposed in the pores of the implant which may then be implanted surgically in a human or animal body. The implant containing cultured cells may encourage tissue growth in and around the implant in vivo.

The present invention also includes a barrier medium for preventing tissue adherence, said barrier medium comprising a polysaccharide foam in accordance with the invention.

In another aspect of the present invention, the polysaccharide foam may constitute a carrier for a beneficial agent formulation. Said beneficial agent formulation may be accommodated within the cells of the foam. Typically the formulation may comprise a beneficial agent and a pharmaceutically acceptable excipient therefor. In some embodiments, the beneficial agent may be a drug which can be administered to a patent transdermally. Typically, the beneficial agent formulation may be included in the aqueous solution of polysaccharide prior to foaming. Alternatively, however, the beneficial agent formulation may be incorporated in the foam after formation; in some embodiments the foam may be immersed in or sprayed with the formulation (which may itself be in solution); in other embodiments the formulation may be dispersed in a solid particulate form in the cellular structure of the foam, or produced by living cells (e.g. microbes) in the foam structure.

In yet another aspect of the present invention, a foam in accordance with the present invention, when wet, may be stored under pressure; typically the wet foam may be stored in a pressurized dispenser such, for example, as a conventional pressurized spray can. In some embodiments, the wet foam may be incorporated with a propellant to assist in subsequent delivery of the foam from the dispenser; said propellant may be any suitable propellant known to a person skilled in the art e.g. a gaseous lower alkane (propane, butane, pentane and the like), nitrogen and carbon dioxide. It will be appreciated that storage under pressure constitutes a convenient method of storing a wet foam prior to use; when required, the foam may simply be dispensed directly to the environment of use.

For example, a wet foamed wound dressing in accordance with the invention may be stored under pressure in a dispenser and dispensed directly onto a patient's skin to treat e.g. abraded skin, burns and open wounds. A wet foam carrying a beneficial agent in accordance with the present invention may be stored and dispensed in the same way to provide rapid therapeutic treatment of a wound or other injury when required. It will be appreciated by a person skilled in the art that a foamed wound dressing or beneficial agent formulation carrier which is stored in a pressurized dispenser may be particularly suitable for the purposes of applying first aid to a patient in an emergency.

Following is a description by way of example only and with reference to the accompanying drawings of methods of carrying the invention into effect.

EXAMPLE 1

Figure 1:
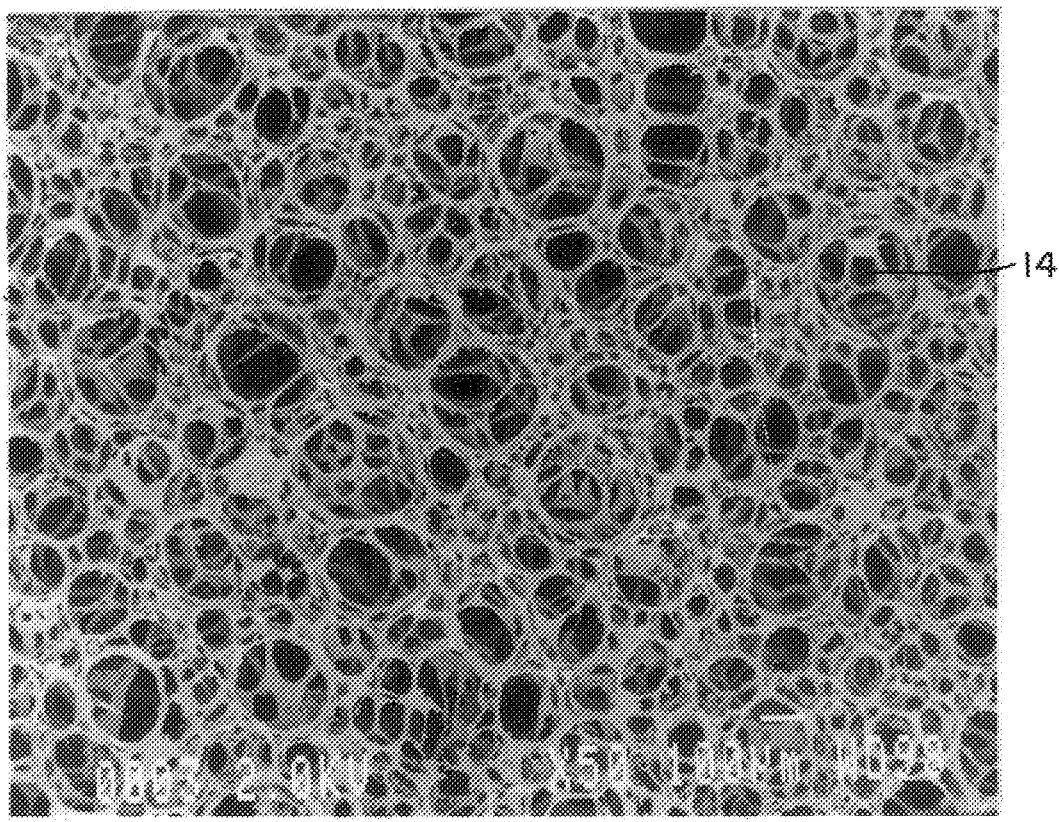
FIG. 1 is a scanning electron microscope ("SEM") photograph showing a surface of a single layer foam produced in accordance with the present invention.

A solution containing 3 wt % of sodium alginate having a viscosity of 1500 centipoise was prepared and to 100 grams of this solution was added 0.1 grams of sodium dodecyl sulfate as a foaming agent. The resultant solution was beaten with a KitchenAid mixer to form a foam. The foam was spread on a metal tray and cross-linked with an aqueous solution containing 5% by weight calcium chloride. The foam was then dried and after drying was found to be 0.05 mm thick and weighing 7 grams per square meter. A scanning electron microscope photograph of the cross-linked foam revealed an open pore structure which was found to have an air permeability of 110 m/min measured at 12.7 mm $H_2O$ pressure.

A portion of the foam produced in the manner described above was converted by placing it in an aqueous solution of hydrogen chloride with a pH of 5 for 30 minutes. The conversation did not affect the gauge weight or pore size, but did change the solubility characteristics. Contact of the non-converted foam with a 1% by weight sodium citrate solution did not affect the structure, whereas the contact of the converted foam with the same 1% by weight sodium citrate solution resulted in a gelation of the foam. This latter action suggested the solubility characteristics were modified by the conversion process.

EXAMPLE 2

A 3"×3" gauze pad comprising a 12-ply 20×12 mesh fabric was used as a substrate for a layer of alginate foam as described in Example 1. The foam was spread on the fabric and cross-linked with a 5% aqueous solution of calcium chloride. The material was then dried and it was found that the cross-linked foam had adhered to the gauze pad to form a coating. The photomicrograph of the resultant structure reveals a thin, 0.05 mm thick foam coating on the gauze pad which had a similar structure as the foam without the substrate described in Example 1.

When the coated pad was placed in an aqueous solution of hydrogen chloride at a pH of 5 for 30 minutes, the calcium structure was converted to a soluble form. Contact of the converted material with sodium citrate once again resulted in gelation of the alginate coating.

EXAMPLE 3

An aqueous solution containing 2 wt % sodium alginate was prepared. To this solution was added 0.2 wt % ammonium stearate (33 wt % in water) as a foam stabilizer and 2 wt % calcium carbonate. The mixture was then well mixed in a KitchenAid mixer to produce a foam having the calcium carbonate dispersed there-through, the foam was drawn in a plastic tray, and 200 ml of 0.1N hydrochloric acid was then added in the tray. As a result of the addition of strong acid, the foam cross-linked. After drying, the foam was found to have a final thickness of 2.1 mm, a density of 0.22 g/cm$^3$ and an air permeability of 6 m/min at a pressure of 12.7 mm H$_2$O. The foam was found to be coagulated uniformly through its thickness.

EXAMPLE 4

A 3% wt aqueous solution of sodium alginate was prepared. To the solution was added 0.85 grams of sodium dodecyl sulphate per 100 grams of alginate solution as a foaming agent. In addition, 2.3 grams of ammonium stearate (33 wt % in water) per 100 grams of alginate solution was added as a foam stabilizer. The resultant solution was beaten with a KitchenAid mixer to form a foam. The foam was spread on a polyester sheet and allowed to air dry. The surface of the dried foam maintained a similar appearance to the wet foam and did not collapse; the foam material in the interior of the foam was found to have "collapsed" and had the appearance of crushed foam. The dried foam was immersed in a 5% wt calcium chloride solution and then allowed to air dry. Once again the dried foam maintained the appearance of the original drawn material. Inspection under an optical microscope revealed the foam was an open-cell structure with fairly uniform pore sizes. The foam had a final thickness of 2.8 mm, a density of 0.05 g/cm$^3$, and a permeability of 90 m/min at 12.7 mm H$_2$O.

EXAMPLE 5

To a solution of similar composition to Example 1 was added 1 gram of anhydrous glycerol per gram of alginate material. The solution was foamed mechanically, drawn into a desired thickness and allowed to air dry. The dried foam was crosslinked using a 5% wt calcium chloride solution and air dried. The resultant foam had a final thickness of 0.25 mm, a density of 0.14 g/cm$^3$ and an air permeability of 100 m/min at 12.7 mm H$_2$O pressure. After 3 months under ambient conditions, the foam had a similar handling ability as a newly formed foam.

EXAMPLE 6

Figure 2:
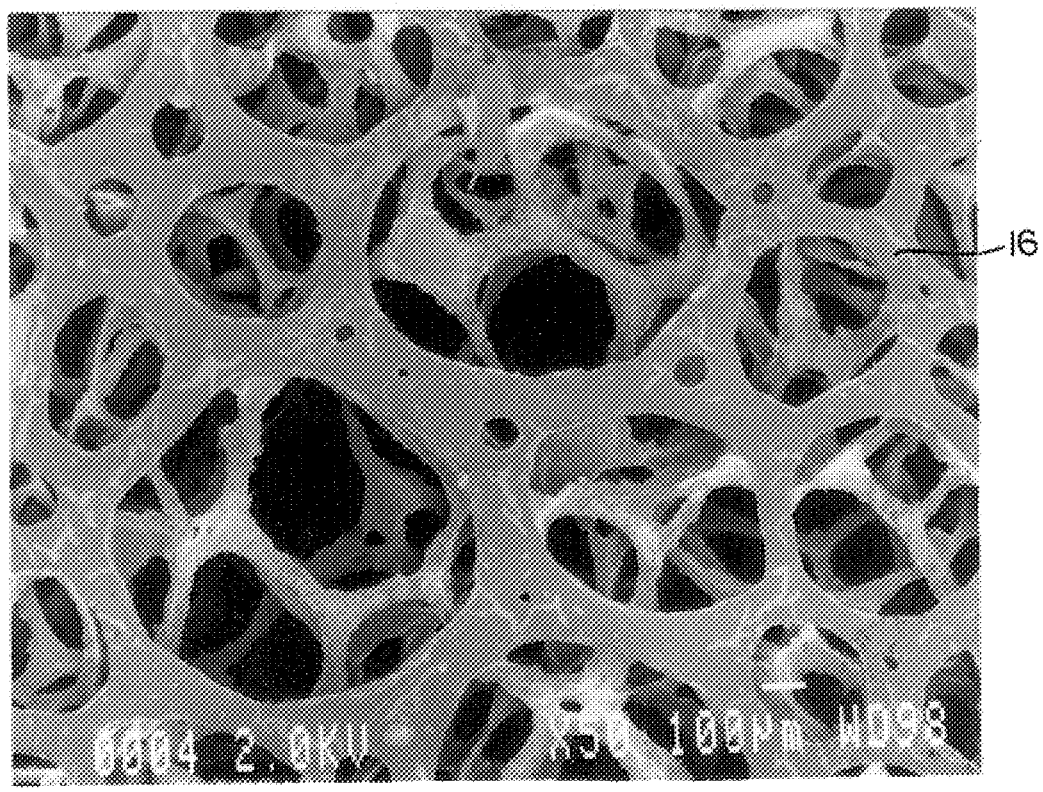
FIG. 2 is an SEM photograph of another surface of the single layer foam of FIG. 1.
Figure 3:
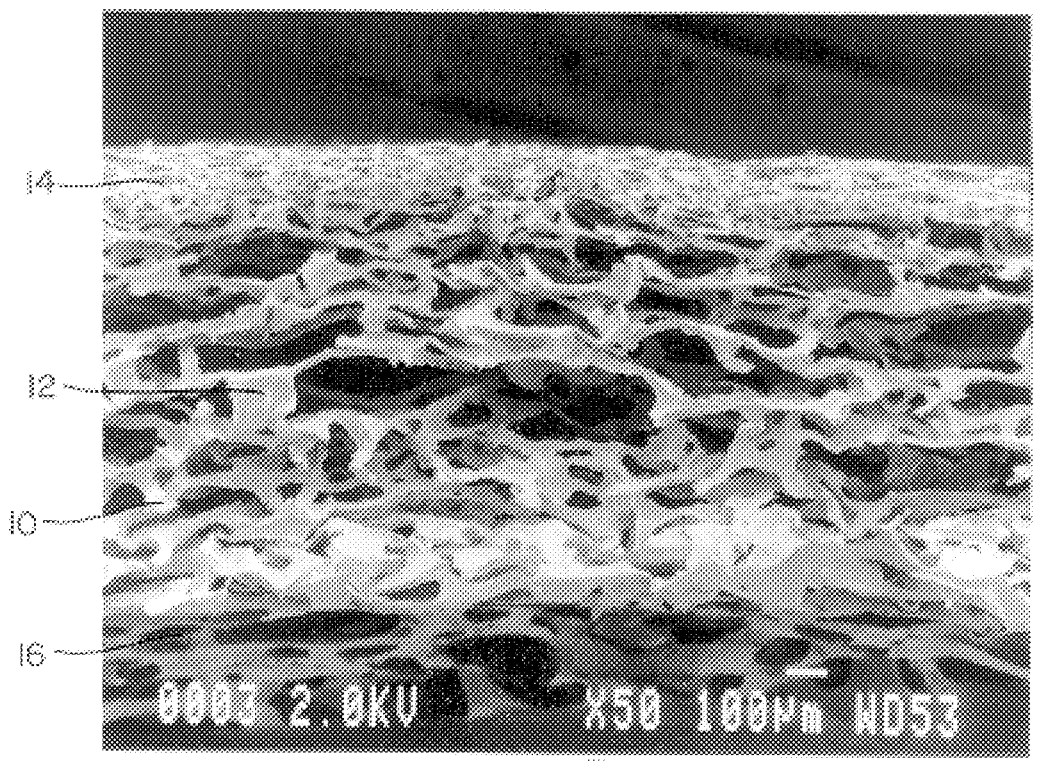
FIG. 3 is an SEM photograph of a cross section through the thickness of the single layer foam of FIGS. 1 and 2.

A single layer alginate foam was produced by a method similar to the method described in Example 4 above. FIGS. 1 to 3 are Scanning Electron Microscope photographs of the resultant dried foam (10). It will be noted that an interior region (12) of the foam is "collapsed" giving the appearance of "crushed" foam, while the surfaces (14, 16) of the foam substantially maintain their pore size and pore size distributions.

EXAMPLE 7

Figure 4:
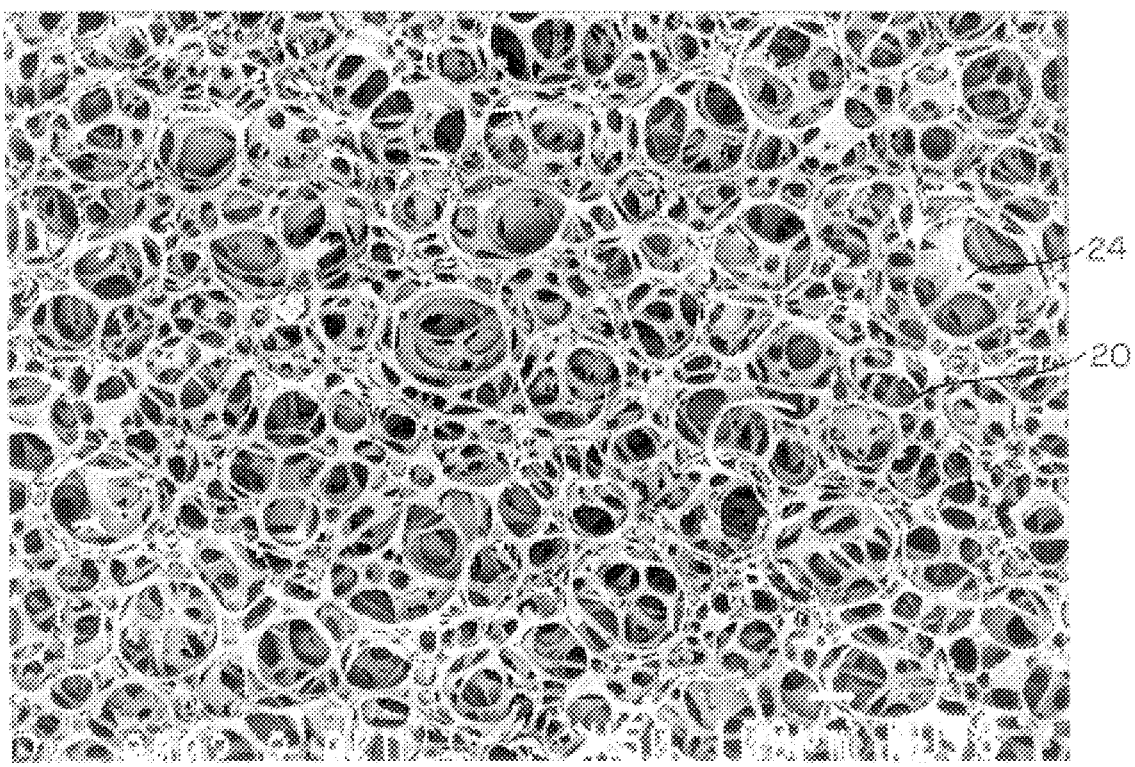
FIG. 4 is an SEM photograph of a surface of a two layer foam produced in accordance with the present invention.
Figure 5:
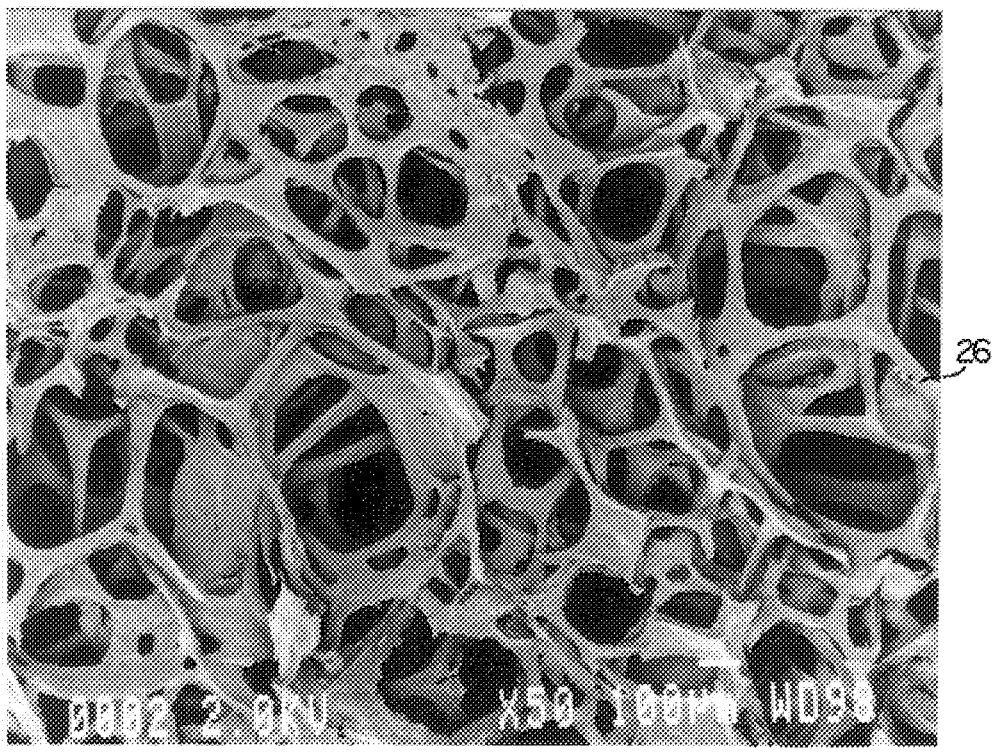
FIG. 5 is an SEM photograph of another surface of the two layer foam of FIG. 4.
Figure 6:
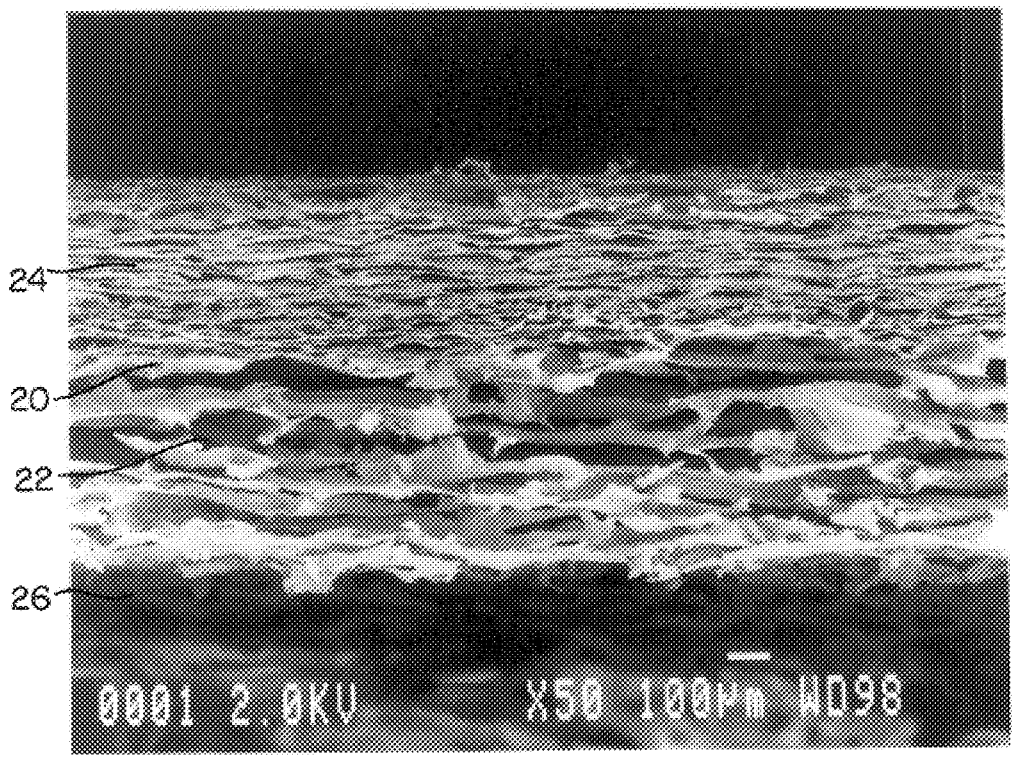
FIG. 6 is an SEM photograph of a cross section through the thickness of the two layer foam of FIGS. 4 and 5.
Figure 7:
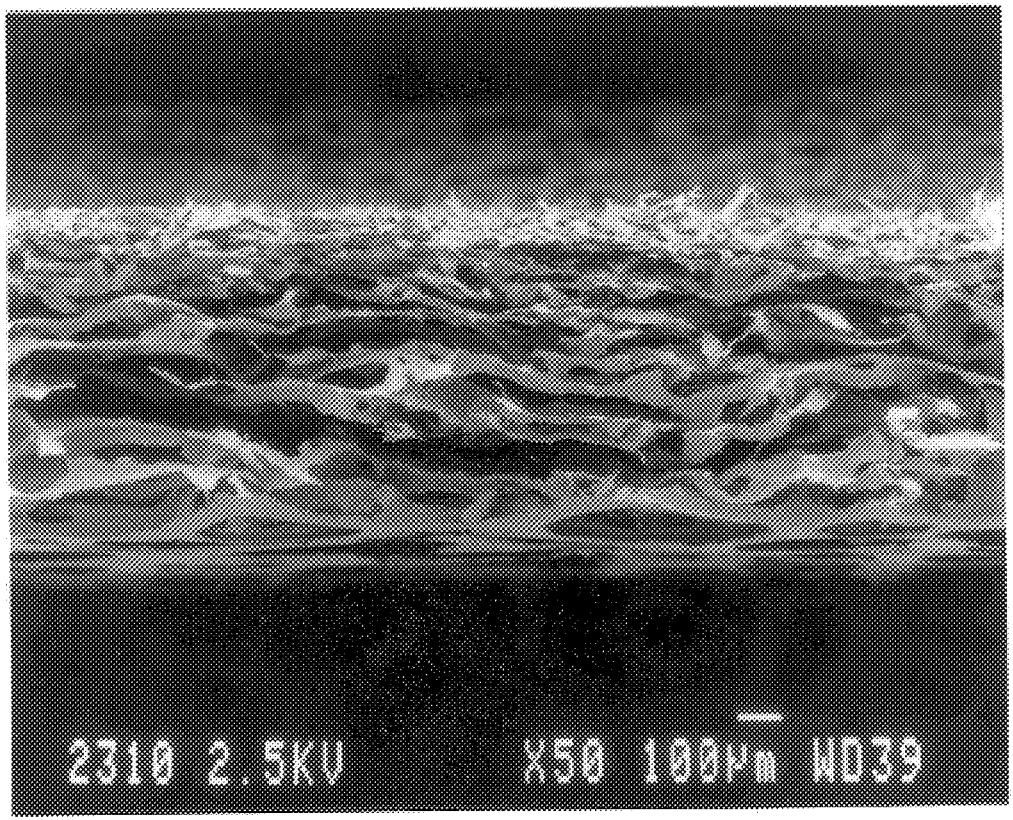
FIG. 7 is an SEM photograph showing the cross-section of a surface of a sodium alginate foam dried in ambient air.
Figure 8:
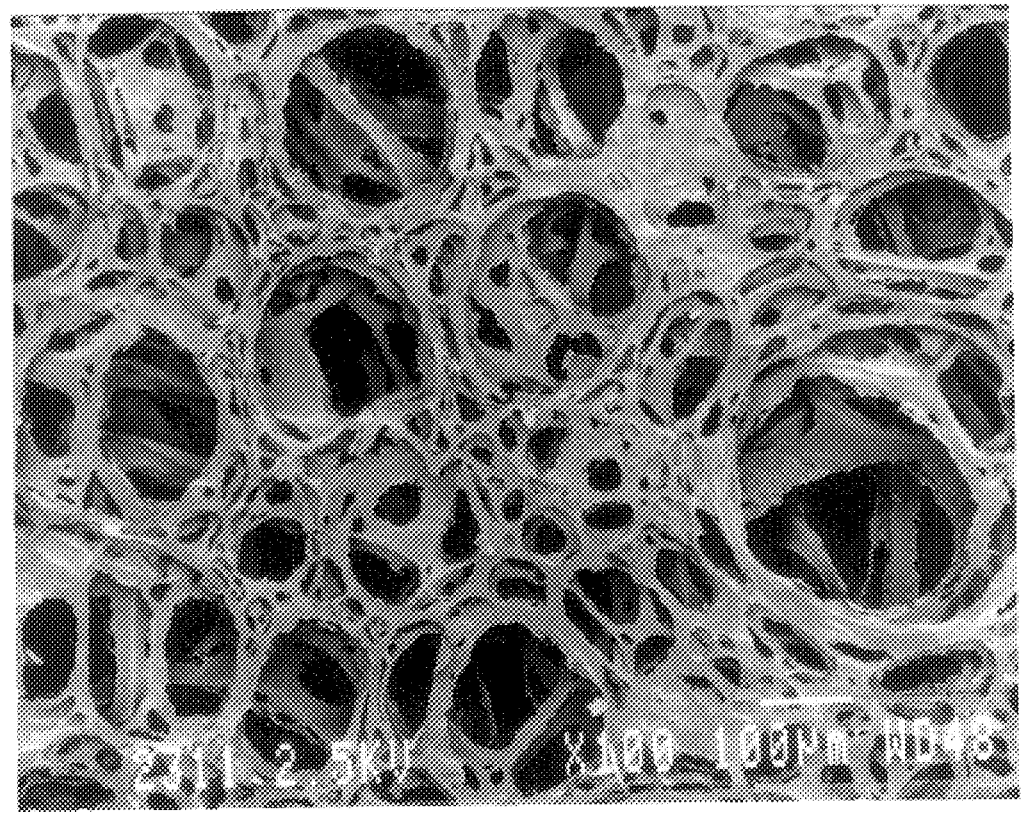
FIG. 8 is an SEM photograph showing the top surface of the sodium alginate foam dried in ambient air.
Figure 9:
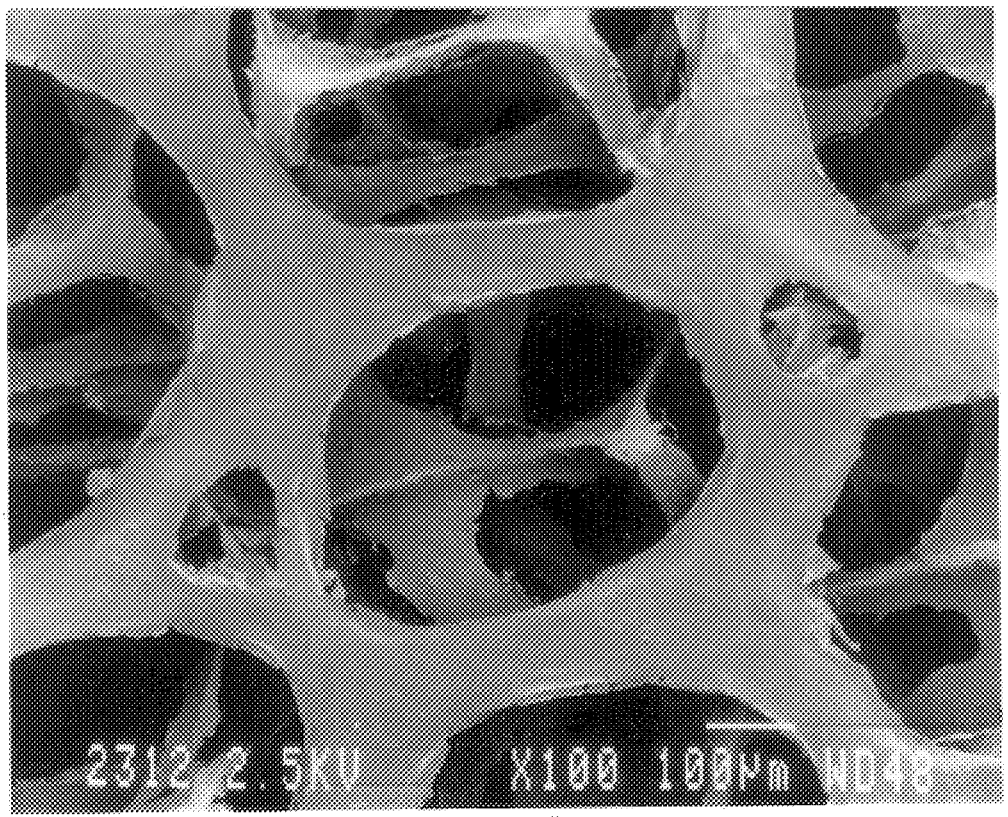
FIG. 9 is a SEM photograph showing the bottom side of a sodium alginate foam dried in ambient air.
Figure 10:
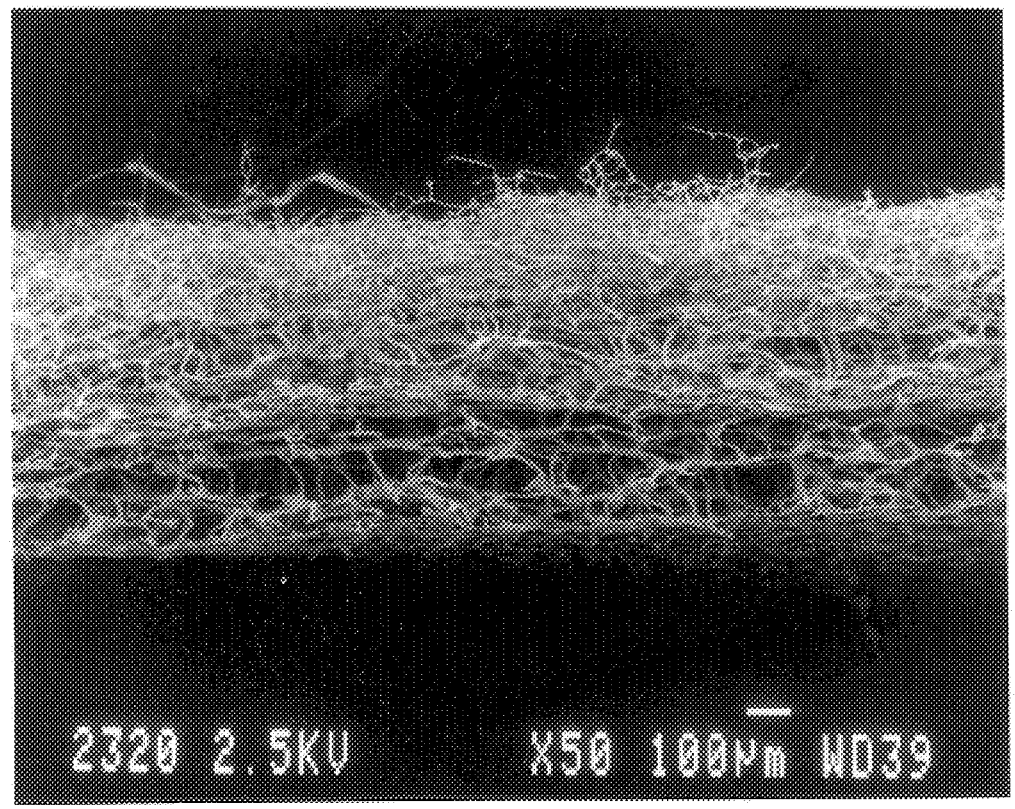
FIG. 10 is a SEM photograph showing the cross section of a sodium alginate foam convection dried in hot air.
Figure 11:
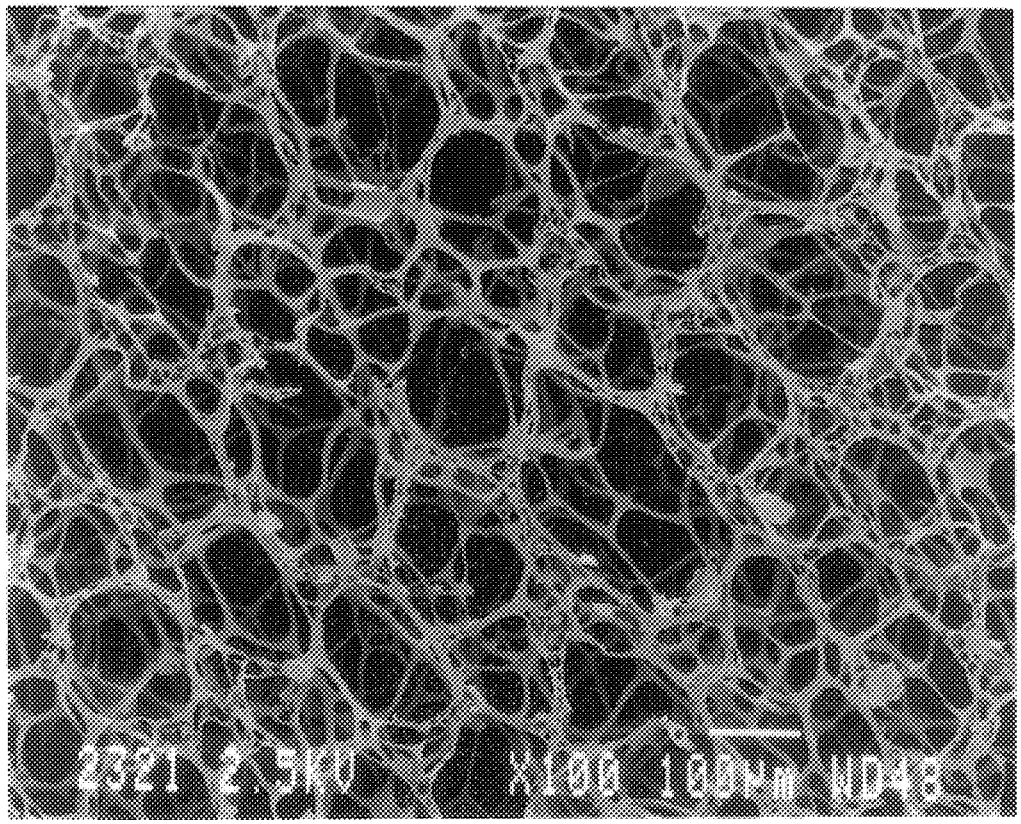
FIG. 11 is a SEM photograph showing the top side of sodium alginate foam convection dried in hot air.
Figure 12:
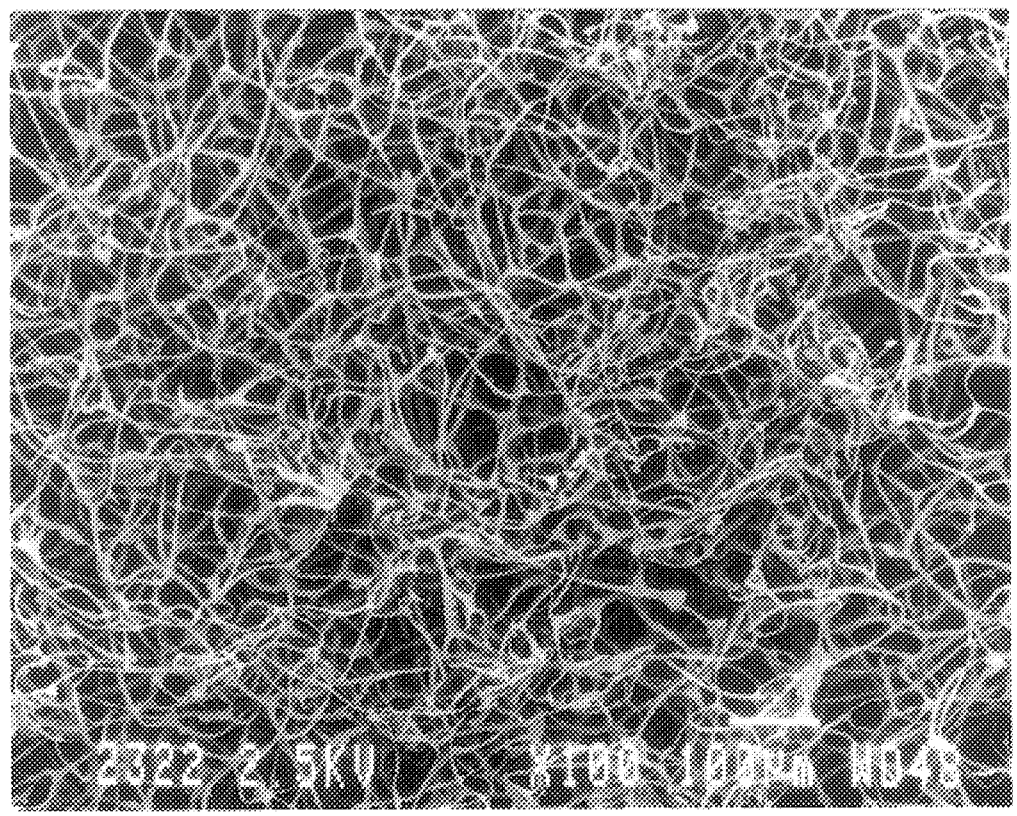
FIG. 12 is a SEM photograph showing the bottom side of sodium alginate foam convection dried in hot air.
Figure 13:
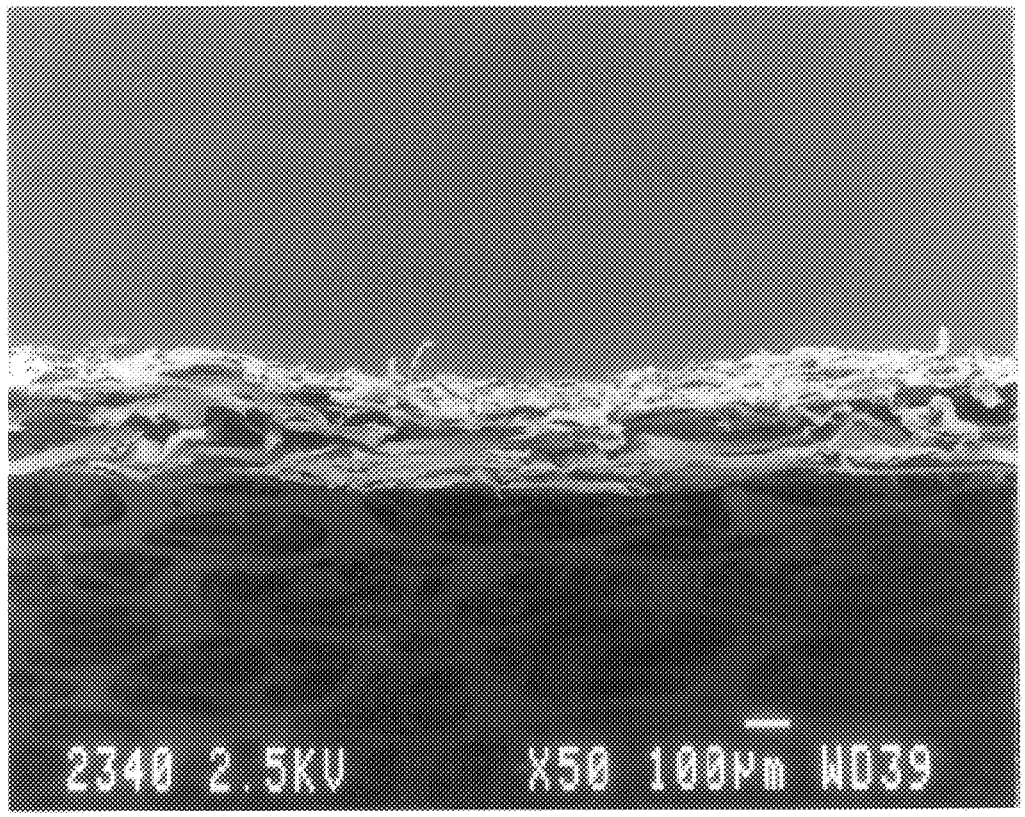
FIG. 13 is a SEM photograph showing a cross section of a calcium/sodium alginate foam dried in ambient air.
Figure 14:
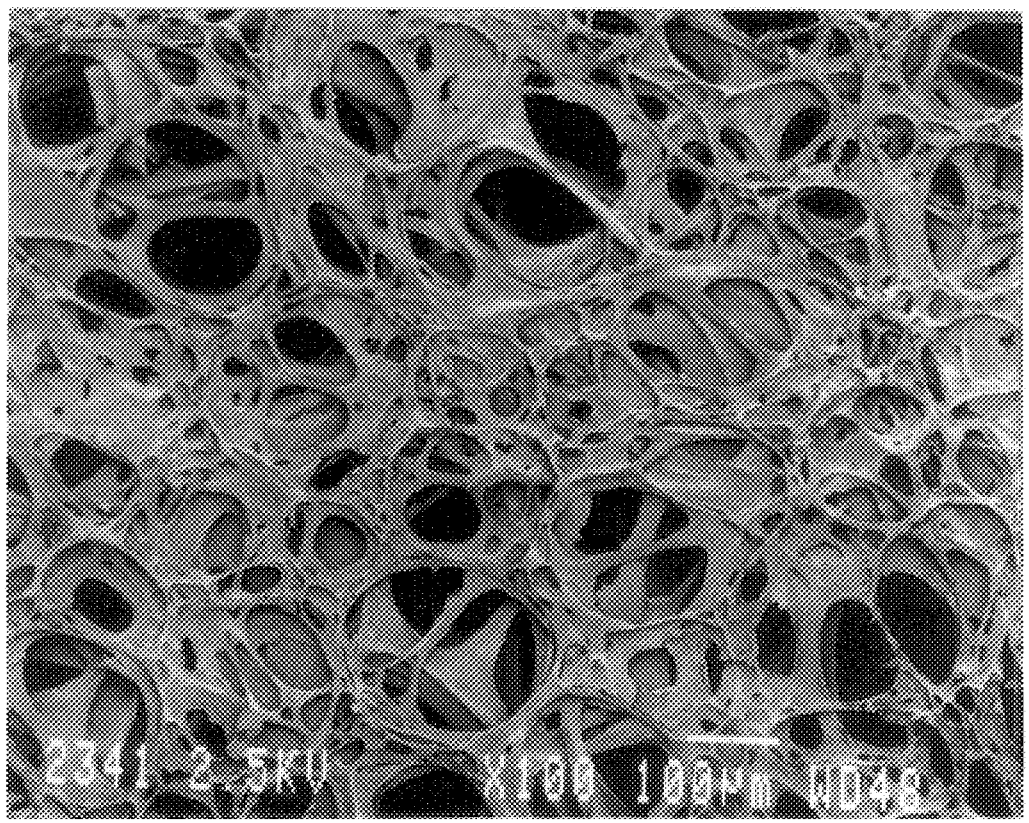
FIG. 14 is a SEM photograph showing a top side of a calcium/sodium alginate foam dried in ambient air.
Figure 15:
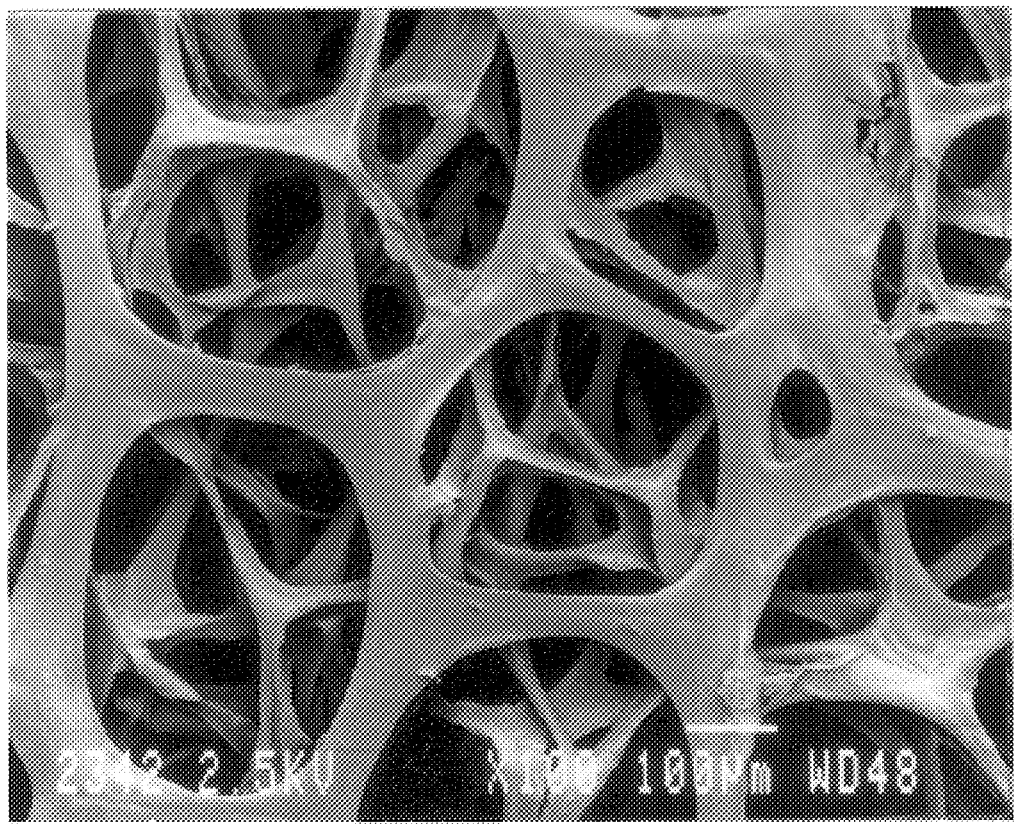
FIG. 15 is a SEM photograph showing the bottom side of a calcium/sodium alginate foam dried in ambient air.
Figure 16:
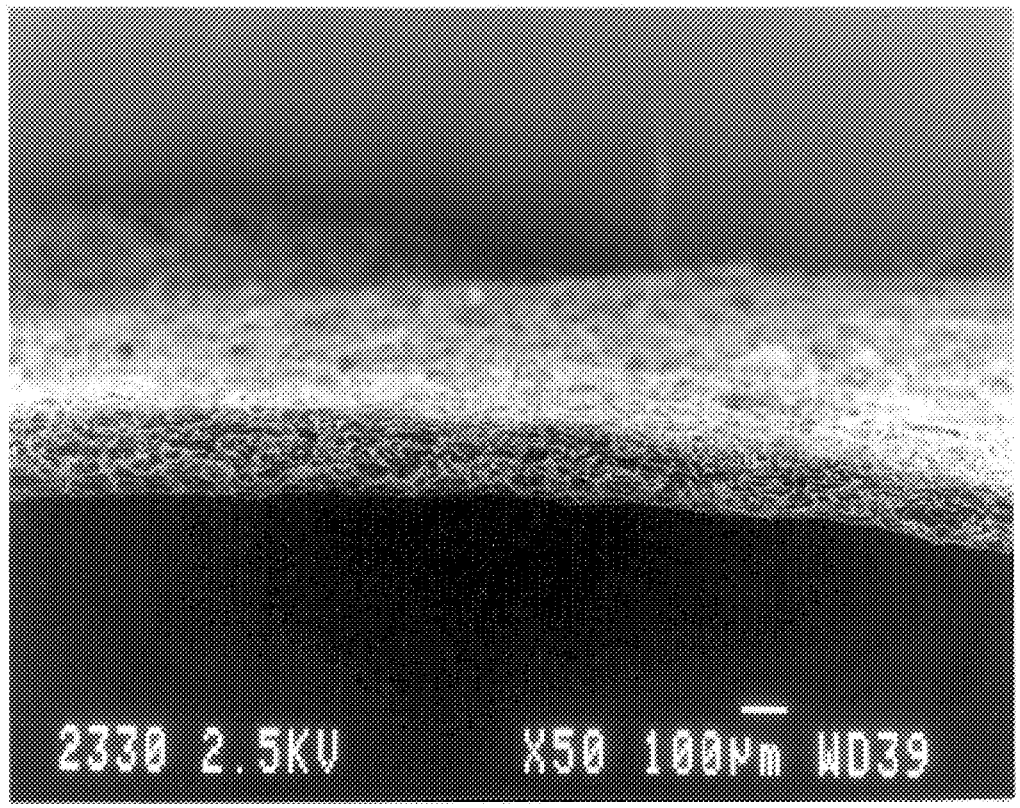
FIG. 16 is a SEM photograph showing the cross section of a calcium/sodium alginate foam convection dried in hot air.
Figure 17:
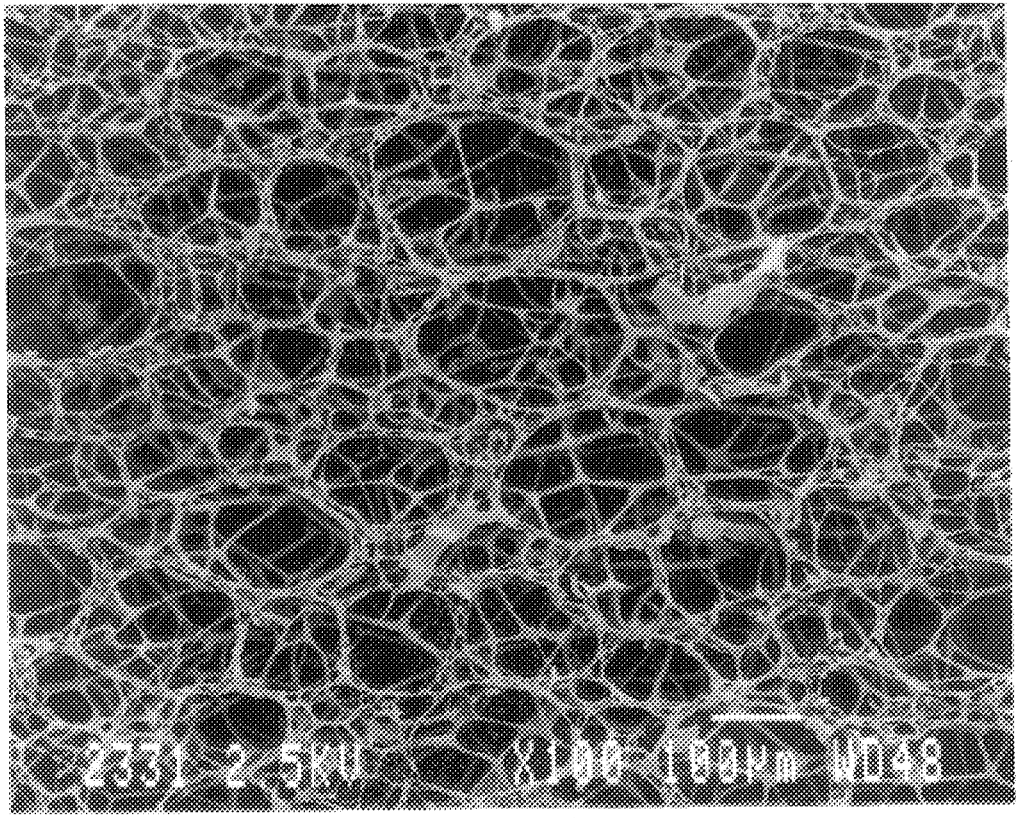
FIG. 17 is a SEM photograph of the top side of a calcium/sodium alginate foam convection dried in hot air.
Figure 18:
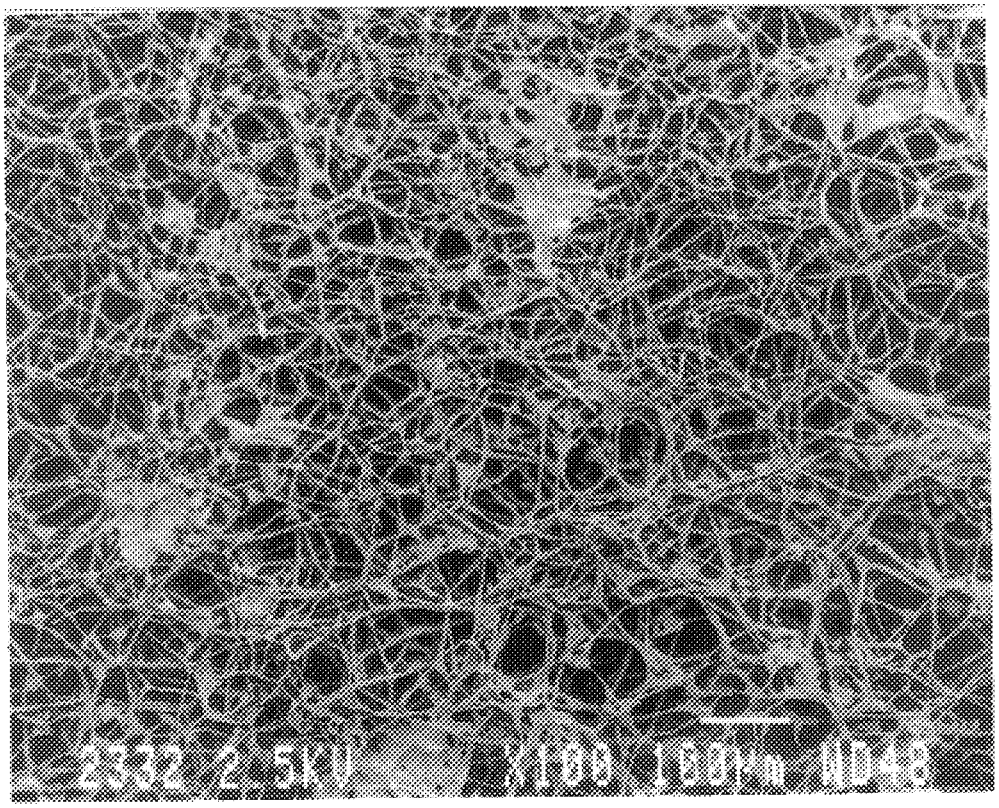
FIG. 18 is a SEM photograph showing the bottom side of a calcium/sodium alginate foam convection dried in hot air.
Figure 19:
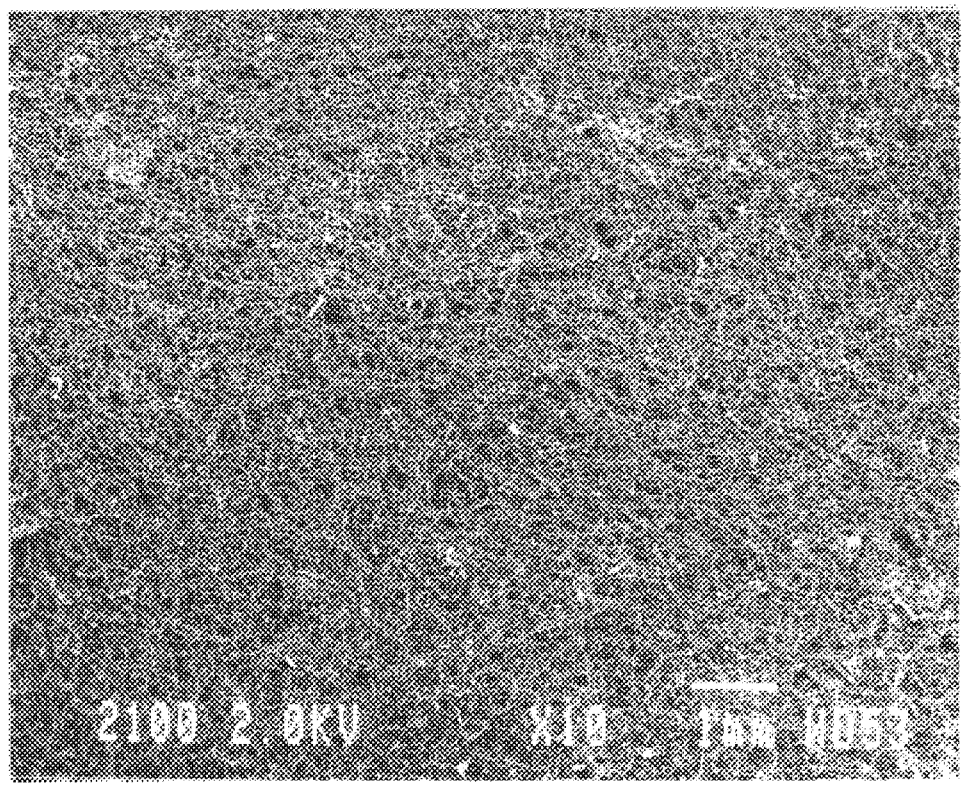
FIGS. 19 and 20 are SEM photographs of the top side of a calcium/sodium alginate foam convection dried in hot air.
Figure 20:
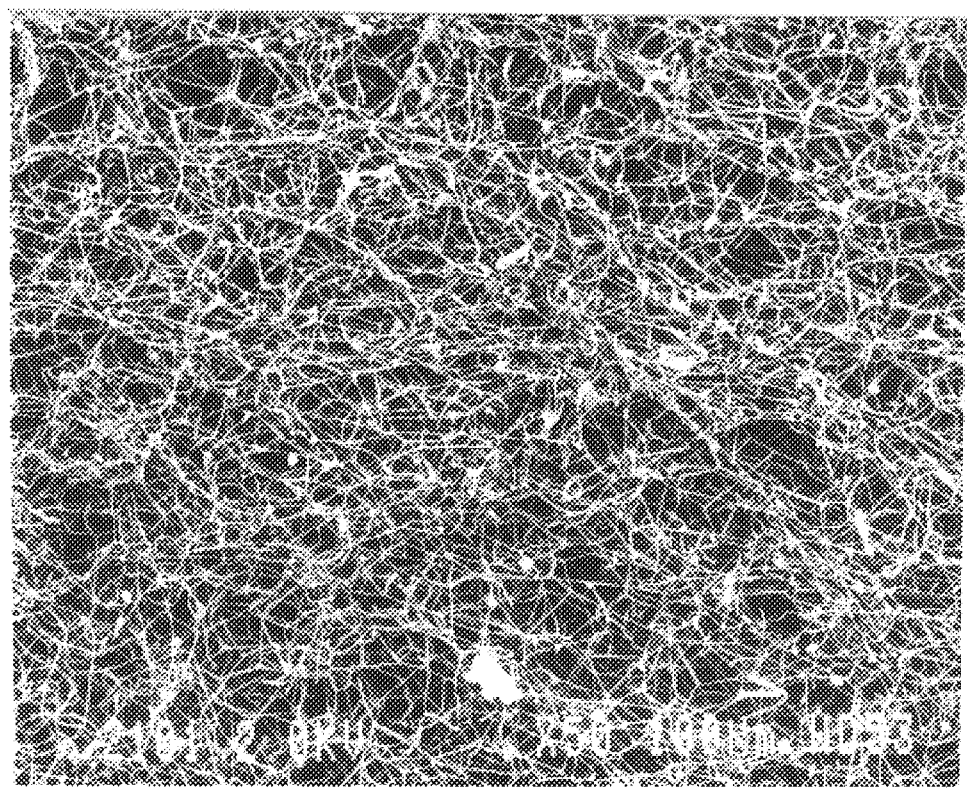
Figure 21:
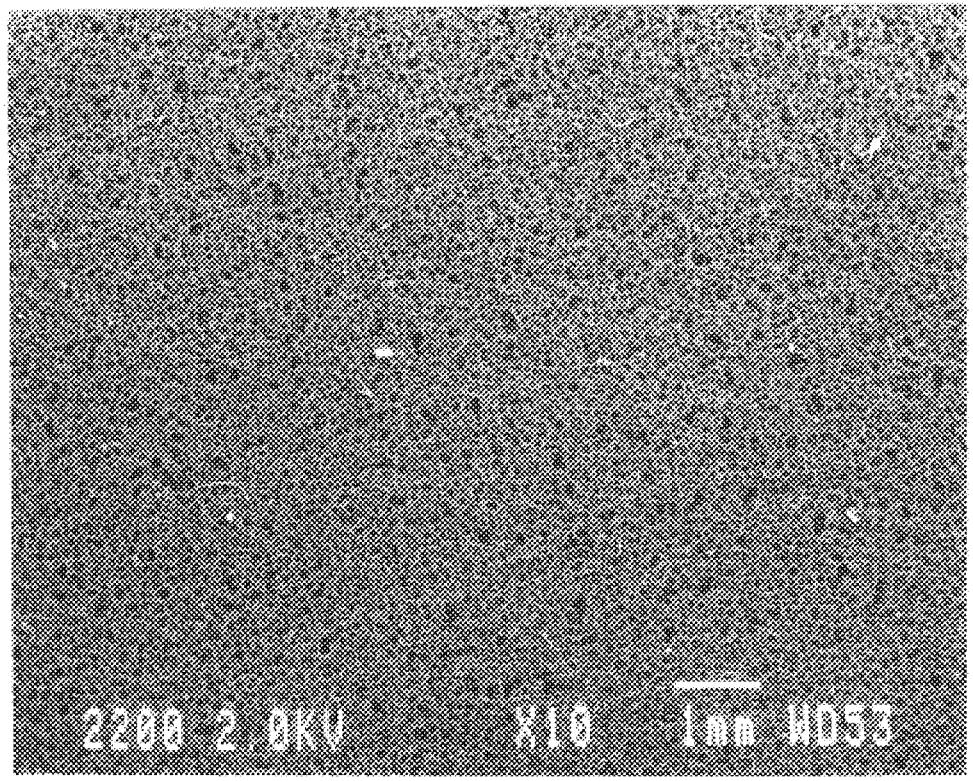
FIGS. 21 and 22 are SEM photographs of the bottom side of a calcium/sodium alginate foam convection dried in hot air.
Figure 22:
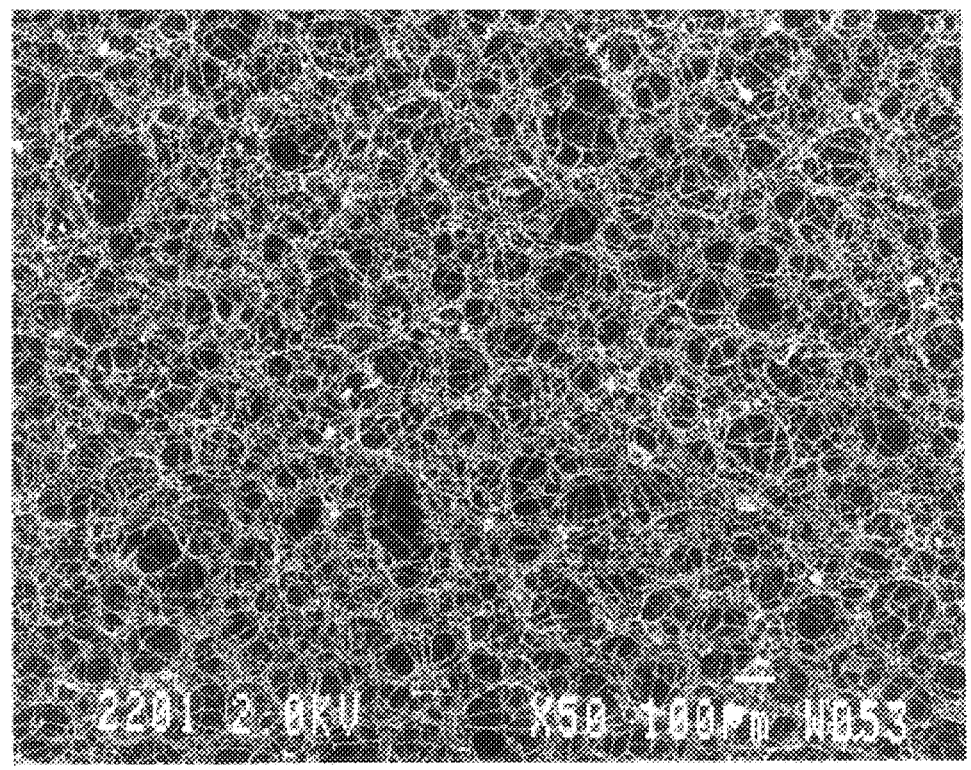
Figure 23:
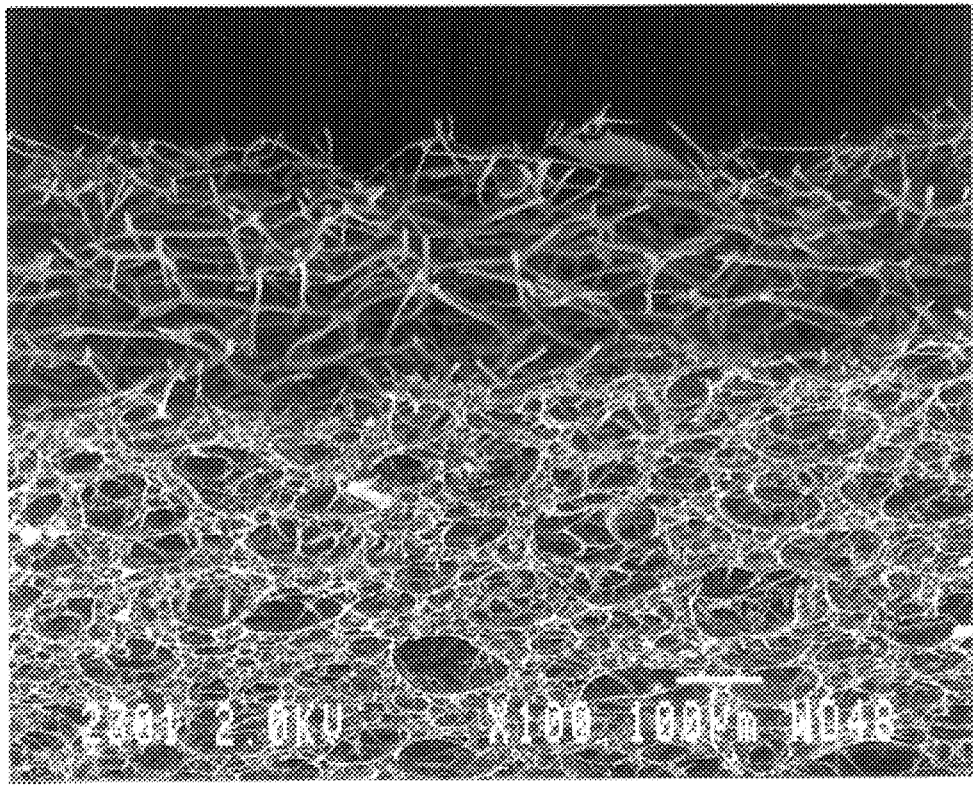
FIG. 23 is an SEM photograph of the cross section of a calcium/sodium alginate foam convection dried in hot air.
Figure 24:
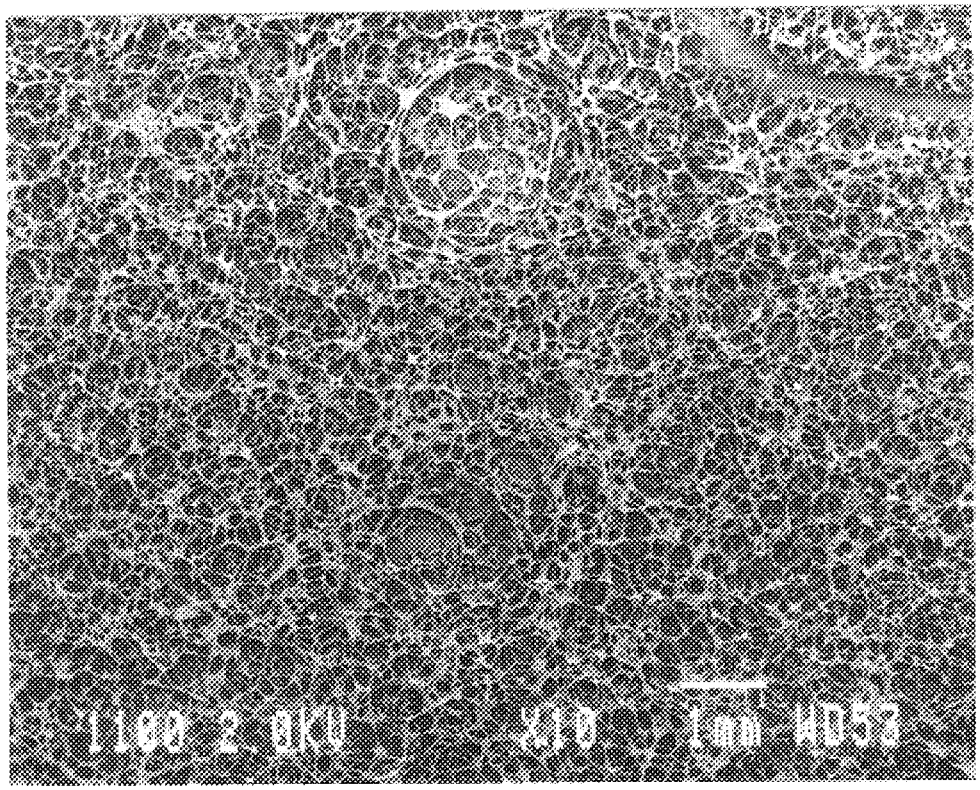
FIGS. 24 and 25 are SEM photographs of the top side of a calcium/sodium alginate foam dried in ambient air.
Figure 25:
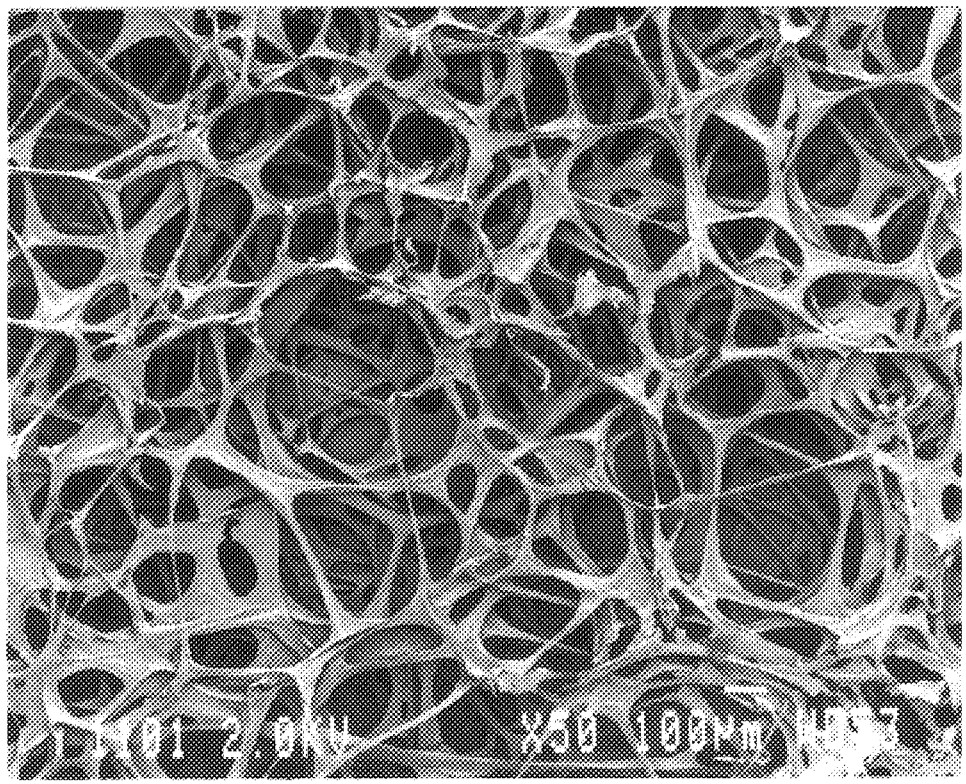
Figure 26:
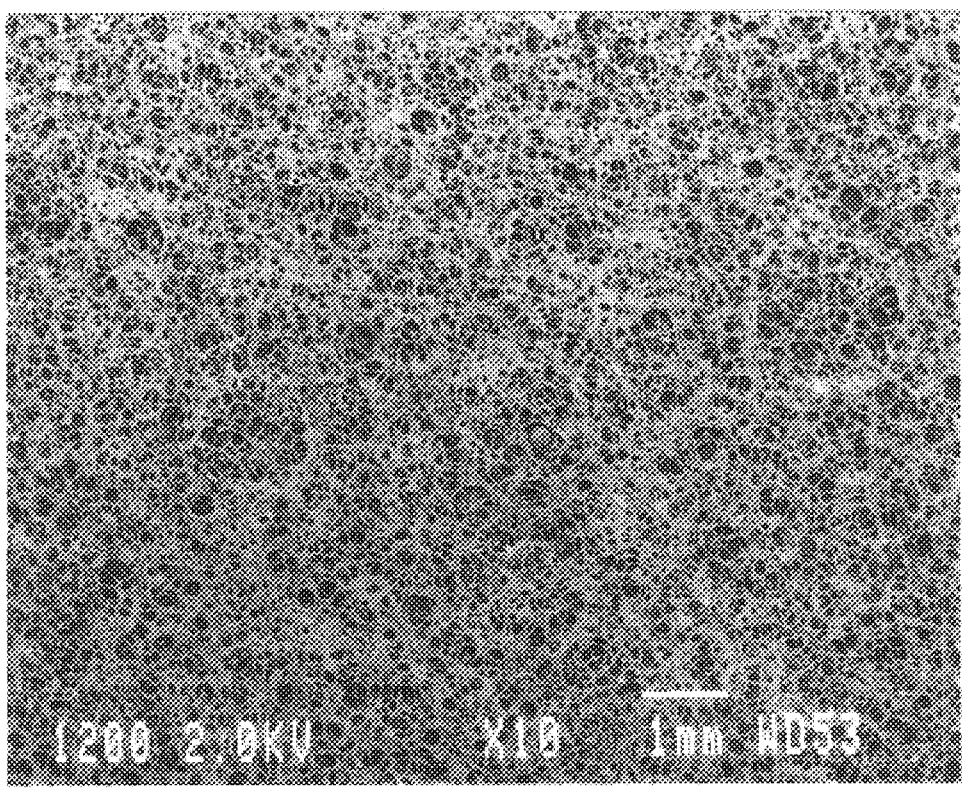
FIGS. 26 and 27 are SEM photographs of the bottom side of a calcium/sodium alginate foam dried in ambient air.
Figure 27:
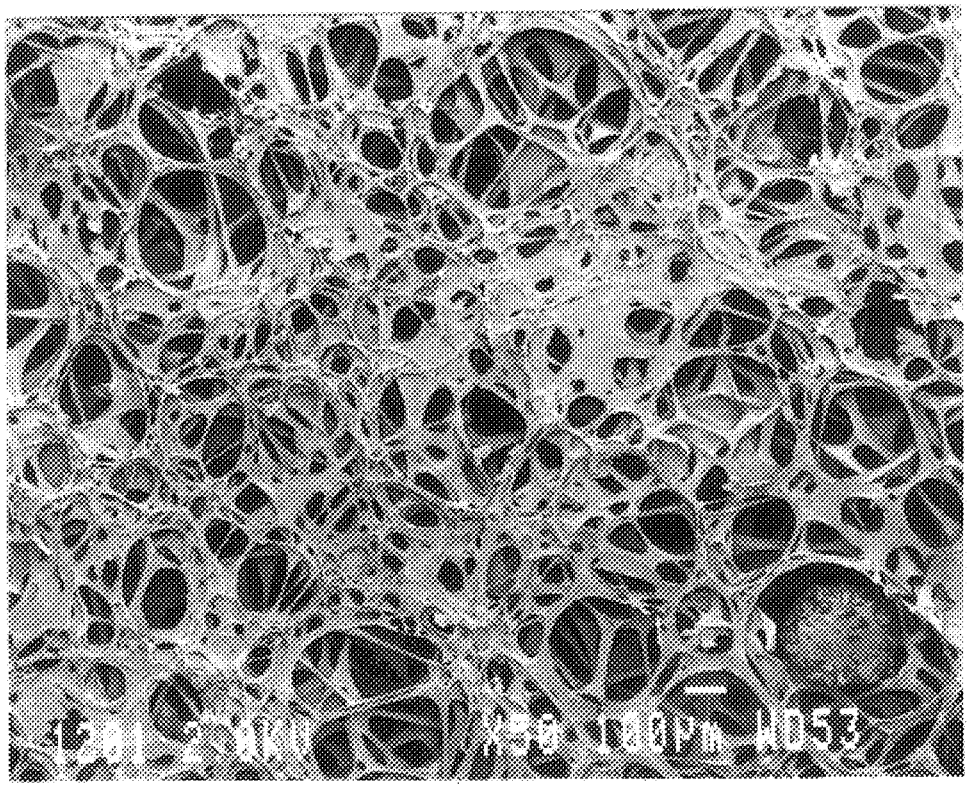
Figure 28:
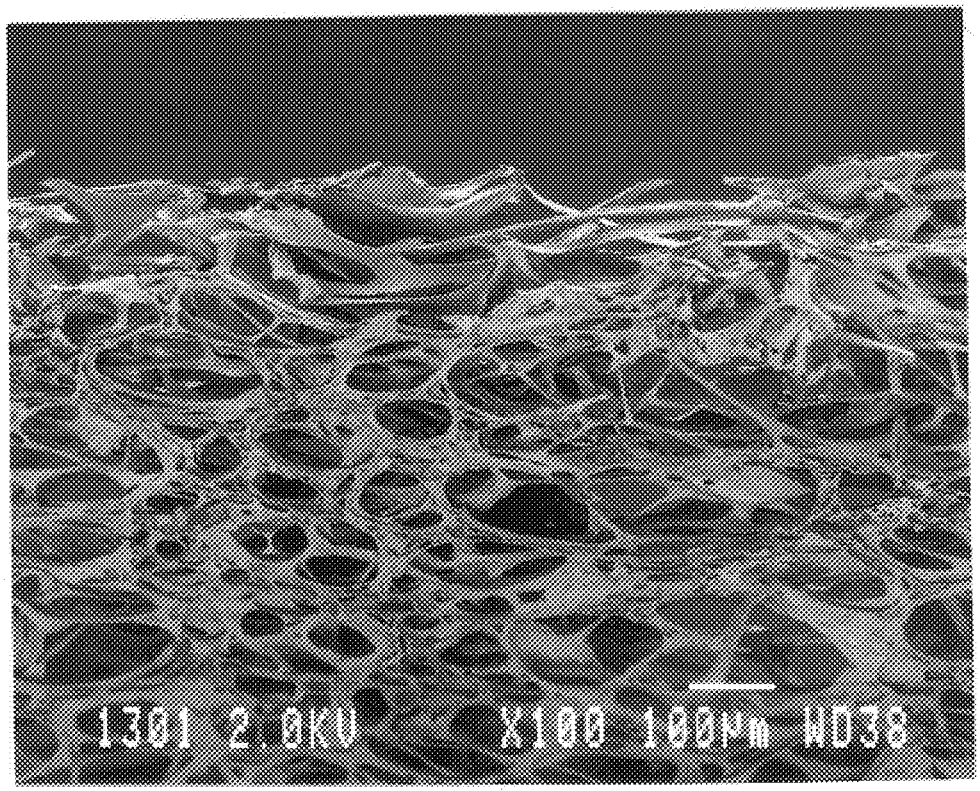
FIG. 28 is an SEM photograph of the cross section of a calcium/sodium alginate foam dried in ambient air.

Another alginate foam layer was made by a method similar to the method of Example 4 above; this foam layer was foamed mechanically in accordance with the invention to have a relatively large mean pore size and dried. A second foam layer controlled to have a relatively smaller mean pore size was then cast on one surface of the first mentioned layer and dried. FIGS. 4 to 6 are Scanning Electron Microscope photographs of the resultant two-layer foam (20). It will be noted that an interior (22) of the foam is "collapsed", while the surfaces (24, 26) substantially maintain their controlled pore sizes and pore size distributions.

EXAMPLE 8

An aqueous solution containing 5 wt % sodium hyaluronate was prepared. To this solution was added 2.7 grams of sodium dodecyl sulphate and 5.3 grams of ammonium stearate (33 wt % in water) per 100 grams of solution. The mixture was well beaten with a KitchenAid mixer to form a foam. The foam was spread onto a polyester sheet and air dried. Inspection under an optical microscope revealed the foam was an open-cell structure with fairly uniform pore size.

EXAMPLE 9

A solution was prepared with 10 grams of 37.5 w/w Hcl and 490 grams water. Fifteen grams of chitosan were added and dissolved in the acid. To the solution were added 1.5 grams of sodium dodecyl sulfate and 15 grams of ammonium stearate (33 wt % in water). The mixture was beaten in a KitchenAid mixer to form a foam which was subsequently drawn to 25 mils thickness and air dried. Inspection under an optical microscope revealed the foam was open-celled and fairly uniform in pore size.

EXAMPLE 10

An aqueous foam of sodium alginate was prepared by mixing the following ingredients in the following proportions in a KitchenAid mixer: 1000 parts by weight deionized water, 30 parts by weight sodium alginate (Protanal LF10/60); 3 parts by weight dodecyl sodium sulfate, and 15 parts by weight ammonium stearate (33 wt % in water). After these ingredients had been beaten in the mixer to form a foam, a sample was removed for purpose of measuring a wet foam density. The wet foam density was determined to be 0.11 grams per cubic centimeter based upon 27.5 grams of foam occupying a volume of 250 cubic centimeters. The wet foam was cast on a horizontal polyester film supported on a flat table top and using a coating blade. The blade depth was set at 0.64 centimeters and the blade width was 28 centimeters. The length of the cast foam was approximately one meter. After the wet foam was cast on the polyester sheet, it was allowed to air dry at ambient room conditions. During drying, no effect was made to circulate air over the surface of the foam. After 48 hours of drying, the foam was examined and found to be dry.

Another batch of wet alginate foam was prepared using the same composition and method cited above. This foam was cast onto a wet laid polyester nonwoven manufactured by the Elk Corporation. The casting was made using a Mathis lab dryer/coater LJF/LTSV, serial number 149292/92092. The equipment utilized a coating blade which has a width of 28 centimeters. The blade depth was set at a half a centimeter. The foam which was cast had a length of approximately 32 centimeters. After casting, the wet foam was inserted into the hot air convection dryer of the Mathis device for a period of 30 minutes. The temperature of the hot air dryer was maintained at 80° C. After a 30 minute drying period, the foam was removed from the hot air convection dryer and allowed to cool to room temperature.

Both of the above dry sodium alginate foams were further processed to produce a calcium/sodium alginate foam. Both foams were immersed in a five percent aqueous calcium chloride solution to form a calcium alginate foam. After immersion in a calcium chloride solution, both foams were immersed in a 5.0 wt % sodium chloride solution for 15 minutes to promote formation of a calcium/sodium alginate foam. After immersion in this sodium chloride solution, the samples were washed in deionized water. The samples were immersed in isopropanol while wet for three minutes and subsequently allowed to air dry.

Calf serum was used to measure serum uptake by both foam samples. Two samples of ambient air dried calcium/ sodium alginate foam were also tested. Each sample had a weight of 0.3 grams and was made by folding a six inch by six inch piece of foam to form an eight ply two inch by two inch piece. The serum was heated to 37° C. in a water bath and introduced to the foam at approximately 1.5 ml dosages using a pipet. The rate of application was controlled by allowing one minute between each application. After six applications, the foam was allowed to sit for another minute. Tweezers were then used to lift the foam and allow any dripping serum to fall free of the foam prior to weighing the foam saturated with serum. The ambient air dried foam samples were found to absorb 3.5 and 3.7 grams of calf serum, for an average calf serum absorption rate of 12.0 grams of serum per gram of alginate.

The two samples of calcium/sodium alginate foam prepared via hot air convective drying subjected to conversion and immersion in isopropanol were also tested for calf serum uptake. Both samples were prepared from six inch by six inch foam pieces plied to two inch by two inch pieces and weighing 0.3 grams. One sample was found to absorb 6.3 grams of calf serum, while the other sample was found to absorb 6.2 grams of calf serum, for an average calf serum absorption rate of 20.8 grams of serum per gram of alginate.

For comparison purposes samples were prepared in which

1. A sodium alginate foam, dried in a forced convection hot air dryer, was immersed in a calcium chloride solution to form a calcium alginate foam, but was not immersed in a sodium chloride solution to convert it to a calcium/sodium alginate foam. Also, the foam was not immersed in isopropanol. The sample was found to absorb 1.3 grams of calf-serum, or 4.3 grams of serum per gram of alginate.
2. A sodium alginate foam, dried in a forced convection hot air dryer, was immersed in a calcium chloride solution to form a calcium alginate foam, and was immersed in a 5.0 wt % sodium chloride solution for fifteen minutes to promote conversion to a calcium/sodium alginate foam. The foam was not immersed in isopropanol. The sample was found to absorb 1.5 grams of calf-serum, or 5.0 grams of serum per gram of alginate.
3. A sodium alginate foam, dried in a forced convection hot air dryer, was immersed in a calcium chloride solution to form a calcium alginate foam, but was not immersed in a sodium chloride solution to convert it to a calcium/sodium alginate foam. The resulting calcium alginate foam was immersed in isopropanol while wet for three minutes and subsequently allowed to air dry. The sample was found to absorb 3.1 grams of calf-serum, or 10.4 grams of serum per gram of alginate.

The data reported above is set forth in Table 1:

TABLE 1

| Alginate Foam | Drying Method | Isopropanol Immersion | Calf-Serum/Absorption (gm. serum/gm. alginate) |
| --- | --- | --- | --- |
| calcium | heated air | no | 4.3 |
| converted | heated air | no | 5.0 |
| calcium | ambient air | yes | 9.4 |
| converted | ambient air | yes | 12.0 |
| calcium | heated air | yes | 10.4 |
| converted | heated air | yes | 20.9 |

EXAMPLE 11

An aqueous foam of sodium alginate was prepared by mixing the following ingredients in the following proportions in a KitchenAid mixer: 1000 parts by weight deionized water, 30 parts by weight sodium alginate (Protanal LF10/60); 3 parts by weight dodecyl sodium sulfate, and 15 parts by weight ammonium stearate (33 wt % in water). After these ingredients had been beat in the mixer to form a foam, a sample was removed for the purpose of measuring a wet foam density. The wet foam density was determined to be 0.12 grams cubic centimeter based upon 30.0 grams of foam occupying a volume of 250 cubic centimeters. The wet foam was cast on a horizontal polyester film using a coating blade. The blade depth was set at 0.64 centimeters. The blade width was 28 centimeters. The length of the cast foam was approximately one meter. After the wet foam was cast on the polyester sheet, it was allowed to air dry at ambient room conditions. During drying, no effort was made to circulate air over the surface of the foam. After 16 hours of drying, the foam was examined and found to be incompletely dry as evidenced by a tacky feel to the hand. The foam was allowed to dry for another 24 hours, resulting in a total drying time of 40 hours. After 40 hours of drying, the foam no longer had a tacky feel to the hand.

A second batch of wet alginate foam was prepared using the composition and method cited above. This foam was cast onto a wet laid polyester nonwoven manufactured by the Elk Corporation. This casting was made on the equipment described in Example 10. The equipment utilized a coating blade which has a width of 28 centimeters. The blade depth was set at a half a centimeter. The foam which was cast had a length of approximately 32 centimeters. After casting, the wet foam was inserted into the hot air convection dryer for a period of 25 minutes. The temperature of the hot air dryer was maintained to 80° C. After a 25 minute drying period, the foam was removed from the hot air convection dryer and allowed to cool to room temperature.

As described above, two dry sodium alginate foam materials were produced via two different drying routes. One was prepared by drying at ambient conditions while the other was prepared by drying with a hot air convection oven. Both of these products were examined via scanning electron microscopy. The results are shown in FIGS. 7 through 12. These Figures show that the ambient air dried foam has considerably larger pores and larger struts than the foam formed by hot air convection drying. In addition, the foam which was formed by hot air convection drying has a more uniform pore size as compared to the ambient air dried foam. Both foams exhibit an open cell structure.

Both of the above dry sodium alginate foams were further processed to produce a calcium/sodium alginate foam. Both dry sodium alginate foams were immersed in a five percent aqueous calcium chloride solution to form a calcium alginate foam. After immersion in a calcium chloride solution, both foams were washed in deionized water. After washing, both samples were immersed in 0.9 wt % sodium chloride solution for 30 seconds to promote formation of a calcium/sodium alginate foam. After immersion in this sodium chloride solution, the samples were washed in deionized water. After washing, the samples were immersed in isopropanol. The samples were then allowed to air dry.

The calcium/sodium alginate foam samples formed by the above process were examined via scanning electron microscopy. The results are shown in FIGS. 13 through 18. The cell sizes of the foam subjected to hot air convective drying are on average smaller than the cell sizes of the ambient air dried foam. Physical measurements were also made on both foam samples. Bulk density of the dried alginate foam is determined by cutting a square or rectangular sample, weighing it, and obtaining a basis weight that is expressed as mass/ area. The thickness of the foams are then measured using a Randall & Stickney gauge with a weight of 10 oz. and measuring area of one square inch. By dividing mass/area by thickness, a density value is determined.

The bulk density of the calcium/sodium alginate foam formed by ambient air drying was 0.13 g/cc. The bulk density of the calcium/sodium alginate foam formed via hot air convection drying was 0.10 g/cc.

In Example 10 above, it was shown that calcium/sodium alginate foams formed via hot air convection drying have higher calf serum absorption than foams formed via ambient air drying. Example 11 demonstrates that the bulk density of foams formed via hot air convection drying are lower than foams formed via ambient air drying. Cell sizes in the hot air convection dried foam are also smaller than the cell sizes of ambient air dried foam.

EXAMPLE 12

An aqueous foam of sodium alginate was prepared by mixing the following ingredients in the following proportions in a four (4) liter KitchenAid mixer: 500 grams deionized water, 3 grams sodium lauryl sulfate, and 15 grams ammonium stearate (33 wt % ammonium stearate in water). The ingredients were mixed at "low" speed while 15 grams of sodium alginate (Protanal LF10/60) were added over several minutes. The ingredients were then mixed to foam the mixture for about 60 minutes on speed number five (5) so that it filled the entire container after 60 minutes.

EXAMPLE 13

Convection Dried Sodium Alginate

About one-sixth of the alginate foamed material prepared in Example 12 was placed on a supporting fabric (30×40×0.3 cm) of Ryton, a needled polyphenylene sulfide nonwoven with a basis mass of 0.057 g/cm$^2$, using a J-blade (28×1.0×4.5 cm) with a gap of five (5) mm. The Ryton fabric is available from Albany International, Gosford, Australia. Using a LJF/LTJV Mathis Lab Dryer/Coater Unit with maximum air distribution impinging above and below the sample, the foam was dried at 90° C. for 20 min, then cooled for 10 min. In total, three (3) coating samples were prepared. Each foamed material was removed from the fabric using a spatula. A small amount adhered to the fabric. The material appeared to exhibit good integrity.

EXAMPLE 13A

An aqueous foam of sodium alginate was prepared using the method in Example 12 and convection dried at different temperatures using the method in Example 13. One sample of the foamed alginate was dried at 120° C. for ten (10) minutes, and another sample was dried at 130° C. for eight (8) minutes. These foams had the same appearance and quality as those alginates that were dried at 90° C. for 20 minutes or 80° C. for 25 minutes.

EXAMPLE 14

Ambient Dried Sodium Alginate

About one-sixth of the alginate foamed material prepared in Example 12 was placed on the supporting fabric set forth in Example 13 using the J-blade of Example 13. The foamed material was dried in a temperature/humidity controlled room at 20° C. and 65% humidity for 45 hrs. In total, three (3) coating samples were prepared. Each foamed material was removed easily from the fabric using a spatula with negligible amount adhering to the fabric. The material did not appear to have good integrity, being quite friable.

EXAMPLE 15

Crosslinking Foamed Sodium Alginate to Calcium Alginate

The convection dried and ambient dried samples prepared in Examples 13 and 14 were placed between two pieces of woven monofilament fabric and immersed in a bath of 20% by weight calcium chloride solution for 15 min. The dimensions of the bath were 30×45×6 cm, holding 2.5 l of liquid. The material was nipped through a hand-cranked rubber-covered pad rolls and immersed again for an additional five (5) min in the calcium chloride solution. The material was then washed three (3) times in a bath of deionized water using gentle agitation, was removed from the bath. The dimensions of the bath were 30×45×6 cm, holding 2.5 l of liquid. The samples were then placed between two plastic frames (25×28×0.4 cm) and two monofilament fabrics and the samples were clamped securely between the monofilament fabrics.

EXAMPLE 16

Conversion of Calcium Alginate to Calcium-Sodium Alginate

Samples in the plastic frames of Example 15 were placed in a bath of five (5) percent by weight sodium chloride solution for 45 sec, were removed, and were placed in a bath of deionized water using gentle agitation. The samples were then removed from the water (excess water allowed to drain) and placed in a bath of isopropanol for time sufficient to insure that the entire foam sample is exposed to isopropanol. The dimensions of the baths were 30×45×6 cm, holding 2.5 l of liquid. Applicants found 20 seconds of exposure time to be long enough. The samples were removed and air-dried for several hours until dry.

EXAMPLE 17

Foam Dry and Wet Strength Properties

The cross-linked, converted, ambient dried foams and the cross-linked, converted, convection dried foams prepared in Examples 12–16 were tested for web strength using conditions described in U.S. Pat. No. 5,197,945, the disclosure of which is incorporated herein by reference. Tensile strength was measured on five ½ inch wide die cut specimens. The gauge length was one inch and the crosshead speed was 10 inches per minute. Wet testing was done on specimens soaked in 0.9% aqueous saline solution for 10 min and then blotted to remove the excess. The maximum load was recorded as the tensile strength. Basis weight was determined by weighing three die cut 1 and ½ inch by 2 inch convective dried specimens and two similarly die cut ambient dried specimens. Table 2 summarizes the test data:

TABLE 2

| Type of Foam | Basis Weight (g/m²) | Dry Strength (Newton) | Dry Strength (N/g/m²) | Wet Strength (Newton) | Wet Strength (N/g/m²) |
|---|---|---|---|---|---|
| Convection dried | 12.6 | 0.648 | 0.051 | 0.320 | 0.025 |
| Ambient dried | 15.6 | 0.570 | 0.037 | 0.127 | 0.008 |
| This data can be compared to the lowest basis weight alginate material in U.S. Pat. No. 5,197,945 and samples of Sorbsan and Kaltostat also tested in the patent: | | | | | |
| 3M Hydroentangled Alginate Nonwoven | 32 | 0.49 | 0.015 | 0.12 | 0.004 |
| Sorbsan[1] | 112 | 0.45 | 0.004 | 0.13 | 0.001 |
| Kaltostat[2] | 160 | 0.71 | 0.004 | 2.14 | 0.013 |

[1]Carded web of alginate fibers marketed as Steriseal Sorbsan ™ surgical dressing by N.I. Medical, Redditch, Worcestershire, England.
[2]Carded and needletacked web of alginate fibers marketed as Kaltostat ™ hemostatic wound dressing by Cair Ltd., Aldershot, Hatt, England.

Strength testing reveals the conductive dried foam is significantly stronger when wet than the ambient dried foam. When compared to alginate nonwoven products described in U.S. Pat. No. 5,197,945, the convective dried foam is stronger dry and wet versus all nonwoven materials on a normalized basis weight. Even when compared on an absolute strength basis, the convective dried foam is stronger dry and wet versus a hydroentangled material that has 2.5 times the basis weight of the foam and a Sorbsan material that has 8.9 times the basis weight of the foam.

EXAMPLE 18

Preparation of Four Ply Calcium-Sodium Alginate Foam

A. Four sheets of foamed sodium alginate (convection dried) were prepared as set forth in Examples 12 and 13. They were layered between two pieces of the Ryton nonwoven fabric and then placed in a platen press (Carver Laboratory Press, Model No. 2518, available from Fred S. Carver, Inc, Menomonee Falls, Wis.) for 30 seconds at 13,000 psi. These mechanically laminated sheets were then treated as set forth in Examples 15 and 16 for the crosslinking and conversion to calcium-sodium alginate. After drying, the sheets appeared to be laminated to each other. SEM photographs indicate that actual chemical crosslinking may not have occurred across each layer. The layers can be pulled apart but not without some strong effort. The surfaces in the pieces that were pulled apart appear to have similar characteristics to the original surfaces of the sample when whole. This would indicate that the layer interfaces have been only minimally affected through the combined mechanical and chemical treatment.

B. The procedure is the same as in A above, except that high pressure was not used. The four sheets were placed together, crosslinked and converted. After drying, lamination had not occurred as the sheets were easily separated.

EXAMPLE 19

Serum Uptake Properties

The cross-linked, converted, ambient dried foams, the cross-linked, converted, convection dried foams, and the four-ply foams prepared in Examples 12–18 were tested for serum uptake properties using conditions described in U.S. Pat. No. 5,197,945, except that specimen size was 3.81 cm×5.08 cm instead of the 2.54 cm×2.54 cm used in the patent. Preweighed samples were immersed in bovine calf serum for 10 minutes at room temperature and then weighted immediately upon removal from the serum. Reported values are the average of three samples. The convection dried foam, ambient dried foam and both of the four ply foams were tested. Table 3 summarizes the test data:

TABLE 3

| Type of Foam | Basis Weight (g/m²) | Serum Uptake (g/m²) | Serum Uptake (g serum/ g alginate) |
|---|---|---|---|
| Convection dried | 12.6 | 0.099 | 78.6 |
| Ambient dried | 15.6 | 0.034 | 21.8 |
| Pressure four ply | 54 | 0.190 | 35.2 |
| No-pressure four play | 59 | 0.508 | 86.1 |
| This data can be compared to the lowest basis weight alginate material in U.S. Pat. No. 5,197,945 and samples of Sorbsan and Kaltstat also tested in the 1945 patent: | | | |
| 3M Hydroentangled Alginate Nonwoven | 32 | 0.07 | 21.9 |
| Sorbsan[1] | 112 | 0.29 | 25.9 |
| Kaltostat[2] | 160 | 0.41 | 25.6 |

[1]Carded web of alginate fibers marketed as Steriseal Sorbsan ™ surgical dressing by N.I. Medical, Redditch, Worcestershire, England.
[2]Carded and needletacked web of alginate fibers marketed as Kaltostat ™ hemostatic wound dressing by Cair Ltd., Aldershot, Hatt, England.

Serum uptake reveals the conductive dried foam absorbs greater serum than the ambient dried foam. When compared to alginate nonwoven products described in U.S. Pat. No. 5,197,945, the convective dried foam absorbs more serum than any of the nonwovens on a normalized basis (grams serum/grams alginate). Even though serum uptake is lower on the pressure laminated sample versus unlaminated convective dried foam, the laminate still absorbs more serum on a normalized basis than any of the nonwovens in U.S. Pat. No. 5,197,945.

EXAMPLE 20

Foam Hand

The calcium/sodium alginate foam samples formed by the above process were examined via scanning electron microscopy. The results are shown in FIGS. 19 through 28. The cell sizes of the foam subjected to hot air convective drying are on average smaller than the cell sizes of the ambient air dried foam. Physical measurements were also made on both foam samples. Bulk density of the dried alginate foam is determined by cutting a square or rectangular sample, weighing it, and obtaining a basis weight that is expressed as mass/ area. The thickness of the foams are then measured using a Shirley thickness gauge with a weight of 3 oz. for a pressure of 0.125 psi. By dividing mass/area by thickness, a density value is determined.

The bulk density of the calcium/sodium alginate foam formed by ambient air drying was 0.078 g/cc. The bulk density of the calcium/sodium alginate foam formed via hot air convection drying was 0.038 g/cc.

The combination of lower bulk density and smaller, uniform cells in the convective dried foam results in a soft, tissue-like appearance and hand, whereas the ambient dried foam has more of a coarser look and a harsher hand.

EXAMPLE 21

Preparation of Laminated Multi-Ply Calcium-Sodium Alginate

The following materials were placed into a four (4) liter Heavy Duty KitchenAid mixing bowl in this order:

250 g deionized water 7.5 g (3.0%) ammonium stearate 1.5 g (0.6%) sodium lauryl sulfate With gradual mixing at low speed, 7.5 g (3.0%) of sodium alginate were added to the above mixture over a five (5) minute period. The mixture was foamed for 30 minutes on speed #4. The foamed material filled the container to approximately half full. About one-third of the foam was spread on a supporting wet-laid, nonwoven, polyester fabric (31×38 cm) using a J-blade with a gap of five (5) mm. Using a Mathis Lab Dryer/Coater Unit (Type LJF/LTJV), the foam was dried at 90° C. for 20 min, then cooled for 10 min. Three dried foam samples were produced in this manner. The individual foam samples were placed in a bath of 20% calcium chloride solution for about 15 minutes. The foams were subsequently placed in a deionized water bath to remove excess calcium chloride. The three crosslinked and washed foam layers were then laid on top of each other in contact with each other. The three sheet composite was sandwiched between two monofilament fabrics and clamped securely. The three (3) sheet composite of calcium alginate was placed in a bath of five percent (5%) by weight sodium chloride solution for about 80 seconds, removed, and placed in a bath of deionized water to remove excess sodium chloride. After washing, the composite was placed in a bath of isopropanol for about 30 seconds. The material was removed from the bath and air-dried for several hours, or until dry. After drying, the supporting fabrics were removed. The end result of the above procedure was the formation of one thick foam laminated from the three layers.

We claim:

1. A method of forming a polysaccharide foam from an aqueous solution of a polysaccharide, consisting essentially of the steps of:

a) forming an aqueous solution of a polysaccharide and a foam stabilizer;

b) introducing a gas into the aqueous solution to form a wet foam;

c) drying the wet foam with heated air to form a dried polysaccharide foam;

d) subsequently cross-linking or coagulating the dried foam to form a water insoluble foam with cross-linking di- or tri-valent cations.

2. The method as set forth in claim 1 wherein the polysaccharide is selected from the group consisting of a water soluble polysaccharide salt, a water soluble alginate, a water soluble hyaluronate, hyaluronic acid, carrageenans, guar gum, and carboxymethyl cellulose.

3. The method as set forth in claim 1 wherein the aqueous solution of polysaccharide contains at least one agent selected from the group consisting of plasticizers, foam modifiers, and foaming agents.

4. The method as set forth in claim 1 wherein polyethylene glycol functionalized with vinyl groups is introduced as a foam modifier and the foam is irradiated to effect polymerization of the functionalized polyethylene glycol forming a polymer network in the foam.

5. The method as set forth in claim 1 wherein the cross-linked foam is converted by treating the foam with an aqueous solution containing solubilizing mono-valent cations so that at least a portion of the cross-linking di- or tri-valent cations in the foam are replaced by the mono-valent cations thereby imparting a degree of solubility in the foam.

6. The method as set forth in claim 5 wherein the converted and cross-linked foam is immersed in a solution containing an alcohol.

7. The method as set forth in claim 1 wherein the cross-linked foam is washed and then redried.

8. The method as set forth in claim 5 wherein the converted and cross-linked foam is washed and then redried.

9. A method of producing an alginate foam from an aqueous solution of an alginate, said foam exhibiting a lower bulk density relative to ambient air-dried foams while exhibiting a greater capacity to absorb calf serum relative to ambient air dried foams, comprised of the steps of:

a) forming an aqueous solution of an alginate;

b) introducing a gas into the aqueous solution to form a wet foam;

c) drying the wet foam with heated air to form a dried alginate foam;

d) cross-linking or coagulating the foam to form a water insoluble foam with cross-linking di- or tri-valent cations;

e) converting the water insoluble foam by treating the foam with an aqueous solution containing solubilizing mono-valent cations so that at least a portion of the cross-linking di- or tri-valent cations in the foam are replaced by the mono-valent cations thereby imparting a degree of solubility in the foam;

f) immersing the converted and cross-linked foam in an alcohol and redrying the foam.

* * * * *